United States Patent [19]

Engelhardt

[11] 3,978,121

[45] Aug. 31, 1976

[54] 5H DIBENZO[A,D]CYCLOHEPTENE DERIVATIVES

[75] Inventor: Edward L. Engelhardt, Gwynedd Valley, Pa.

[73] Assignee: Merck & Co., Inc., Rahway, N.J.

[22] Filed: Apr. 11, 1975

[21] Appl. No.: 567,165

Related U.S. Application Data

[60] Division of Ser. No. 297,710, July 25, 1963, which is a continuation-in-part of Ser. No. 215,770, Aug. 9, 1972, abandoned, which is a continuation-in-part of Ser. No. 140,223, Sept. 25, 1961, abandoned, which is a continuation-in-part of Ser. No. 120,835, May 24, 1961, abandoned.

[52] U.S. Cl............................................. 260/551 C
[51] Int. Cl.²....................................... C07C 125/08
[58] Field of Search ................................ 260/551 C

[56] References Cited
UNITED STATES PATENTS

| | | | |
|---|---|---|---|
| 2,985,660 | 5/1961 | Judd et al. | 260/570.8 |
| 2,996,503 | 8/1961 | Sprague et al. | 260/847.1 |

FOREIGN PATENTS OR APPLICATIONS

| | | | |
|---|---|---|---|
| 1,109,166 | 6/1961 | Germany | 260/570.8 |
| 858,187 | 1/1961 | United Kingdom | 260/570.8 |
| 858,188 | 1/1961 | United Kingdom | 260/570.8 |

OTHER PUBLICATIONS

Derwent Reports, vol. 187, Group 3A, p. 3, 5/13/1960.
Belgium Patent Report I, vol 68B, pp. 620–621, Oct. 18, 1960.
Derwent Belgium Patent Report, vol. 61B, p. 632, 2/15/1960.

*Primary Examiner*—Allen B. Curtis
*Attorney, Agent, or Firm*—Harry E. Westlake, Jr.; James A. Arno; William H. Nicholson

[57] ABSTRACT

Compounds of 5H dibenzo[a,d]-cycloheptenes and 10,11-dihydro-5H-dibenzo[a,d]cycloheptenes which are substituted at their 5-carbon atom with an N-cyanoaminopropyl or an N-cyanoaminopropylidene radical.

7 Claims, No Drawings

5H DIBENZO[A,D]CYCLOHEPTENE DERIVATIVES

This is a division of application Ser. No. 297,710 filed July 25, 1963, now U.S. Pat. No. 3,922,305, which is a continuation-in-part of application Ser. No. 215,770 filed Aug. 9, 1962 and abandoned July 29, 1963, which in turn is a continuation-in-part of application Ser. No. 140,223 filed Sept. 25, 1961 and abandoned Apr. 26, 1963 which in turn is a continuation-in-part of application Ser. No. 120,835 filed May 24, 1961 and abandoned Nov. 8, 1962.

This invention relates to new derivatives of dibenzocycloheptenes and to processes for making them. More particularly, the invention includes 5H-dibenzo[a,d]-cycloheptenes and 10,11-dihydro-5H-dibenzo[a,d]cycloheptenes which are substituted at their 5-carbon atom with an aminopropyl or an aminopropylidene radical. The amino entity may be either primary or secondary and if secondary, the substituent may be either a lower alkyl or alkenyl radical having up to 6 carbon atoms, cycloalkyl having up to 8 carbon atoms or an aralkyl radical. The dibenzocycloheptene nucleus may be further substituted. The invention also includes the intermediates used for obtaining these products. Also included are derivatives such as acyl derivatives which yield the active compound under physiological conditions.

The novel compounds of the invention may be represented by the general formulae

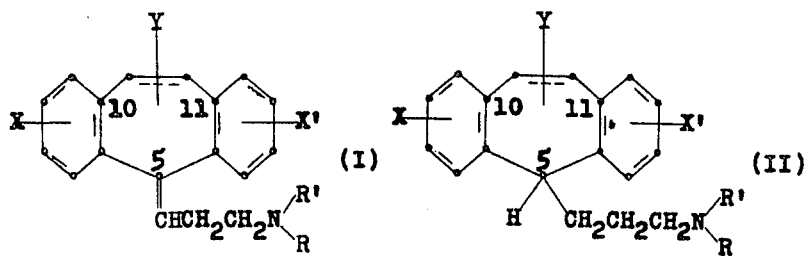

in which R' may be hydrogen or a cyano radical; R may be hydrogen or an alkyl or alkenyl radical having up to 6 carbons, either straight or branched chain, or cycloalkyl having up to 8 carbons or aralkyl groups such as benzyl; Y may be hydrogen or halogen, preferably bromine or chlorine; X and X' are similar or dissimilar and are selected from hydrogen, an alkyl group having up to 6 carbon atoms, an alkenyl group having up to 6 carbon atoms, a perfluoroalkyl group having up to 4 carbon atoms, a phenyl or a substituted phenyl radical, an acyl group having up to 4 carbon atoms, a perfluoroacyl group having up to 4 carbon atoms, amino, an alkylamino group having up to 4 carbon atoms, a dialkylamino group having up to 8 carbon atoms, an acylamino group having up to 4 carbon atoms, a perfluoroacylamino group having up to 4 carbon atoms, an alkylsulfonylamino group having up to 4 carbon atoms, halogen (fluorine, chlorine, bromine or iodine), hydroxyl, an alkoxyl group having up to 4 carbon atoms, a perfluoroalkoxyl group having up to 4 carbon atoms, cyano, carboxy, carbamoyl, an alkylcarbamoyl group having up to 5 carbon atoms, a dialkylcarbamoyl group having up to 9 carbon atoms, a carbalkoxy group having up to 6 carbon atoms, mercapto, an alkylmercapto group having up to 4 carbon atoms, a perfluoroalkylmercapto group having up to 4 carbon atoms, an alkylsulfonyl group having up to 4 carbon atoms, a perfluoroalkylsulfonyl group having up to 4 carbon atoms, sulfamoyl, an alkylsulfamoyl group having up to 4 carbon atoms, or a dialkylsulfamoyl group having up to 8 carbon atoms. More than one of these substituents may be on each benzenoid ring. The compounds may have substituents on the propyl or propylidene chain such as lower alkyl radicals, preferably having from 1 to 4 carbon atoms.

The dotted line between the 10 and 11 carbon atoms indicates that the compounds may be saturated or unsaturated at this location, the saturated compound being identified by the 10,11-dihydro designation.

The compounds represented by the above formulae wherein R' is hydrogen are useful in the treatment of mental disorders since they are anti-depressants and serve as mood elevators or psychic energizers. For this purpose, the daily dosage is within the range of 5 mg. to 250 mg., preferably taken in divided amounts over the day. The compounds are preferably administered in the form of their acid addition salts and these salts are included in the scope of this invention. The compounds represented by the above formulae wherein R' is a cyano radical are useful as intermediates in the preparation of the active compounds.

The compounds I and II differ from each other in that the side chain of compounds I is attached to the nucleus by a double bond. Because of this a process for making compounds I will not be suitable for making compounds II.

To obtain the primary amines of compounds I, it is necessary to employ a different method from heat suitable for obtaining the primary amines of compounds II. For those primary amines of compounds I, the following general method may be followed:

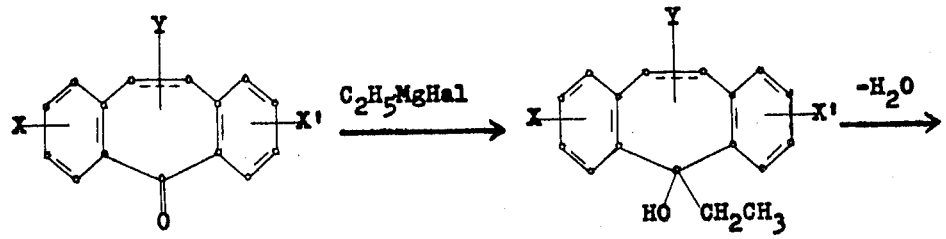

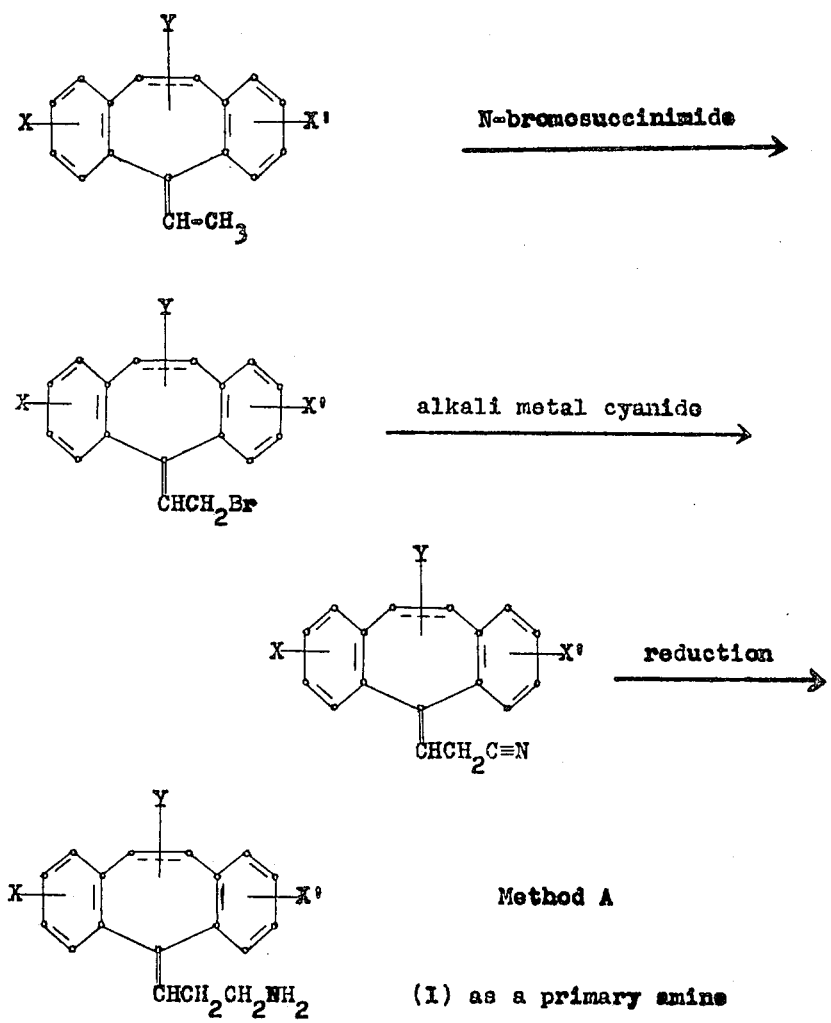

Method A (I) as a primary amine

This method A begins with the known ketone which may be prepared by using the process described by A. C. Cope et al., entitled "Cyclic Polyolefins, XV, 1-methylene-2,3,6,7-dibenzocycloheptatriene," appearing in J.A.C.S. 73, 1673–1678 (1951). Or the starting compounds, and particularly those having substituents on the benzene rings may be made by following the teachings of T. W. Campbell et al. in an article entitled "Synthesis of 2'-acetamido-2,3:6,7-dibenzotropilidene and 2-acetamido-9,9-dimethylfluorene," appearing in Helv. Chim. Acta 36, 1489–1499 (1953). The preparation of the starting compounds having a bromine substituent in either the 10 or 11 positions may be done as described by W. Treibs and H. J. Klinkhammer, Chemische Berichte 84, 671–679 (1951). The preparation of the starting compounds having a chlorine substituent in either the 10 or 11 positions may be done as described in the examples hereinafter.

Method A involves the attachment of an ethylidene chain to the 5-carbon of the nucleus and its subsequent expansion to a propylidene chain having a terminal amino group. The Grignard reagent and the reaction using it are conventional, an inert solvent such as ether is used and the reaction is completed at refluxing temperature. The Grignard adduct is hydrolyzed in the usual manner but it is preferable that it be under approximately neutral conditions such as produced by the addition of ammonium chloride solution. The dehydration step which next follows is carried on preferably by a chemical dehydrating agent such as acetyl chloride, acetic anhydride or trifluoroacetic anhydride which can subsequently be removed by evaporation. N-bromosuccinimide is used for the next step as it is a selective brominating agent and avoids adding bromine to the olefinic linkage. This bromination is preferably carried on at the refluxing temperature of a low boiling inert solvent such as benzene. A substantial excess of N-bromosuccinimide is to be avoided, particularly with compounds of the 10,11-dihydro series. The resulting succinimide precipitates and is removed.

The substitution of the cyanide group for the bromine will occur at room temperature but to hasten it heat is preferably applied. The resulting cyanoethylidene derivative in method A is then isolated by evaporation of the solvent and is then subjected to the reduction step. To avoid simultaneous reduction at the aliphatic double bond, it is best to use a chemical reducing agent such as lithium aluminum hydride in the presence of anhydrous ether. After hydrolysis as by the addition of a caustic alkali solution, the other layer is recovered and the product obtained from it by distillation.

The primary amine which is so obtained in method A can readily be converted to a secondary amine type of compounds I by the following reactions:

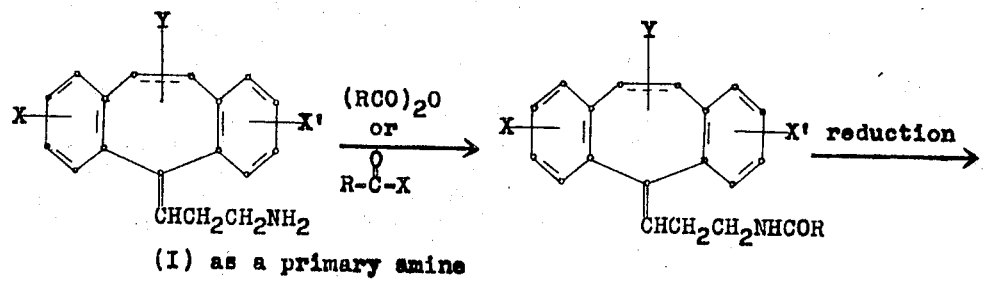

(I) as a primary amine

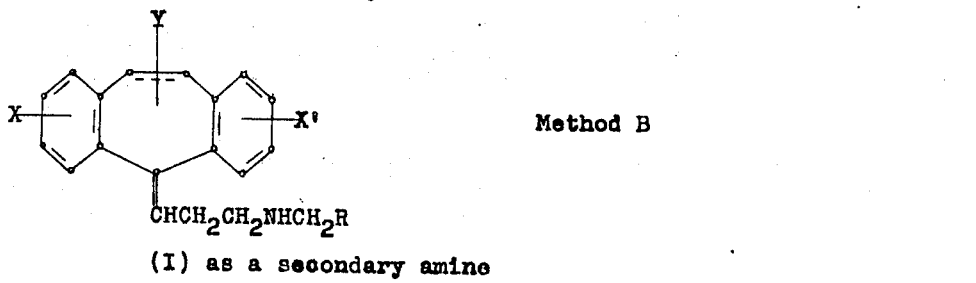

(I) as a secondary amine

Method B

In method B, R can be alkyl, alkenyl or phenyl.

The conversion to the amide is readily carried out by the addition of an acyl halide or anhydride, such as acetic anhydride. This is carried on at room temperature with stirring or by heating. The amide is isolated by removal of the excess acylating agent and the reduction is carried out by the use of a metal hydride as explained above to avoid reduction of the olefinic double bond.

As noted above, method A is useful to obtain compounds I having an olefinic linkage to the side chain. To obtain the compounds of type II, the following series of reactions may be carried out:

In method C, R may be an alkyl or an aralkyl radical.

Method C, in general, involves the initial attachment of an alkoxy or aralkoxy propyl radical at the 5-carbon of the nucleus by a Grignard reaction, the simultaneous reduction of the 5-hydroxy compound and conversion of the alkoxy or aralkoxy group to an iodo radical and then the replacement of this iodo radical with an amino group.

The ketone used as the starting material in method C is the same as that used in method A. It is condensed according to conventional procedures with a Grignard reagent having a terminal ether group. R is preferably a lower alkyl radical having up to 6 carbons. The resulting Grignard adduct is hydrolyzed preferably under neutral conditions as by using an ammonium chloride

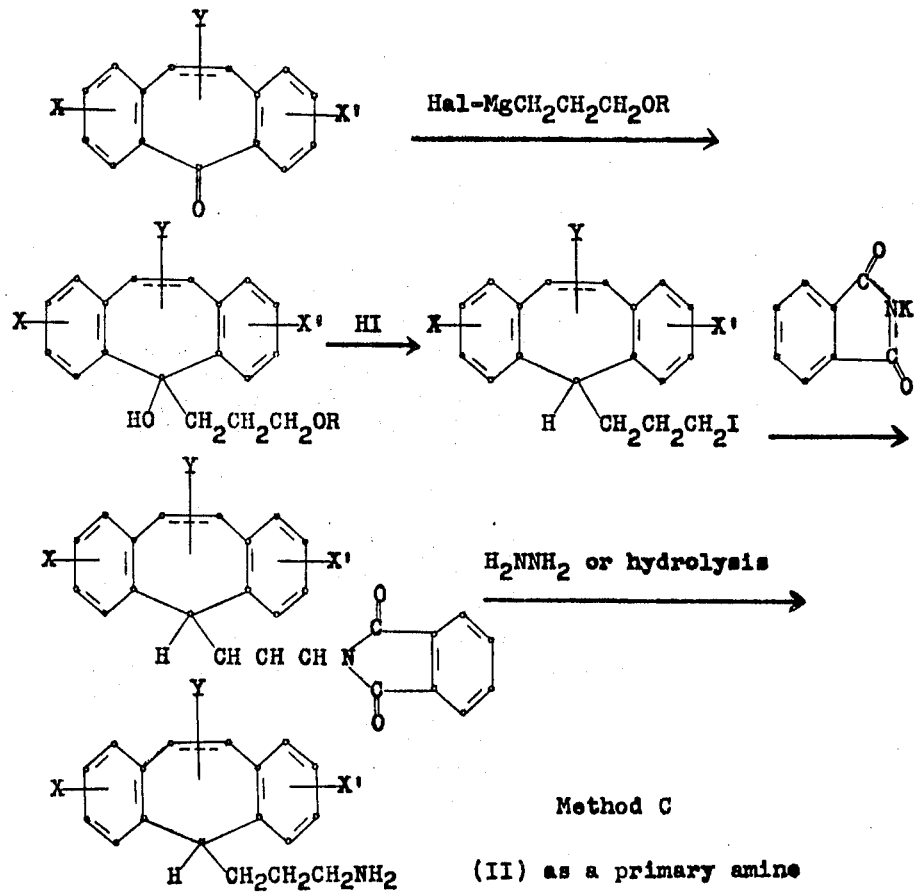

Method C (II) as a primary amine solution. The resulting product is recovered from the solvent by evaporation and is treated with hydriodic acid in the presence of a solvent such as acetic acid or acetic anhydride. The iodinated compound is extracted into a solvent such as benzene and recovered therefrom by evaporation of the solvent. The addition to this iodo compound of the potassium phthalimide is carried on with a solvent such as dimethylformamide and after the complete addition, slight heat may be applied to increase the reaction rate. The phthalimido compound is isolated by extraction.

The subsequent reaction with hydrazine hydrate is carried on in methanol or ethanol and heat may be applied up to the refluxing temperature to hasten the reaction. The phthalhydrazide is separated and the primary amino compound II is recovered from the solution. Instead of employing hydrazinolysis, the phthalimido compound can be converted to the amine by hydrolysis.

This produces the aminopropyl compounds II as a primary amine, and they can be converted to a secondary amine by the following procedure:

linked together through an alkylene chain to form a cyclic ketone. The reaction is carried out in a solvent such as benzene or toluene and heated to refluxing temperature. The resulting alkylidene or cycloalkylidene aminopropyl compound is then recovered by evaporating off the solvent and it is reduced by catalytic hydrogenation to the resulting secondary aminopropyl compound when Y is hydrogen. When Y is halogen, the reduction may be accomplished with a metal hydride as described in mmethod B. Instead of isolating the intermediate compound when Y is hydrogen, the primary amine and the selected carbonyl compound can be dissolved in a suitable solvent such as a lower alcohol, and catalytic hydrogenation carried out.

The primary amine II may also be converted to the secondary amine II by following method B. Likewise, the primary amine I may be converted to the secondary amine I by following method D.

The foregoing methods for preparing the secondary amines I and II are especially suited to those cases where groups larger than methyl are present. Where methyl- or ethylaminopropylidene and methyl- or

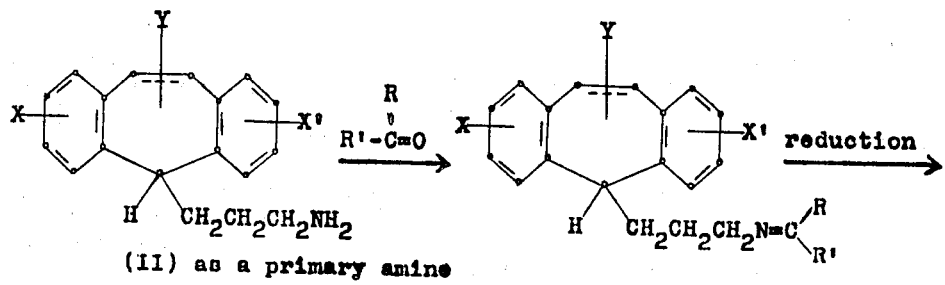

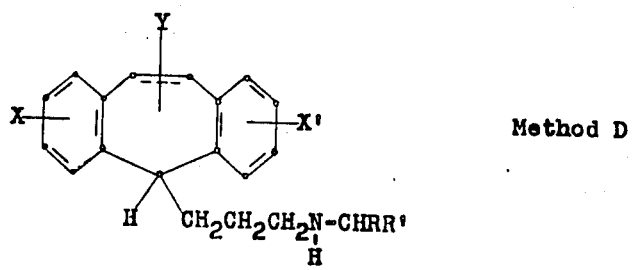

Method D

In method D, the primary amine II is combined with a ketone or an aldehyde of the above structure wherein R' is hydrogen or a lower alkyl radical and R may be hydrogen, alkyl and cycloalkyl. R and R' may also be ethylaminopropyl substituents are desired, they are conveniently prepared from the corresponding dialkylamino compounds by treatment with a cyanogen halide. This monodealkylation process as applied to compounds I and II may be represented as follows:

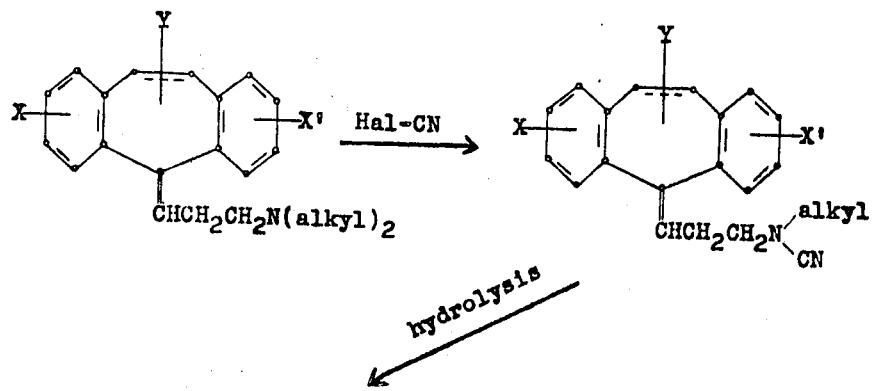

-continued

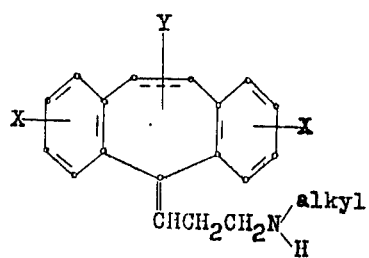

Method E (I) as a secondary amine

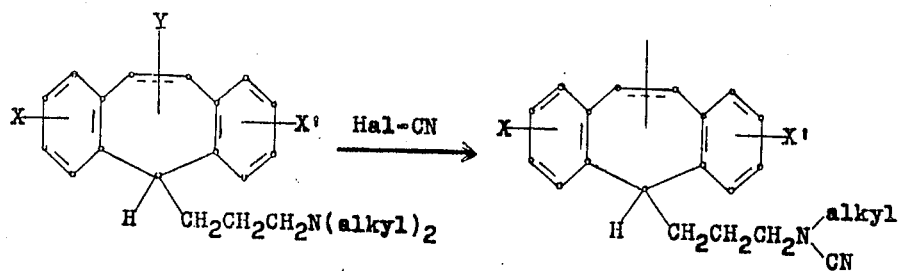

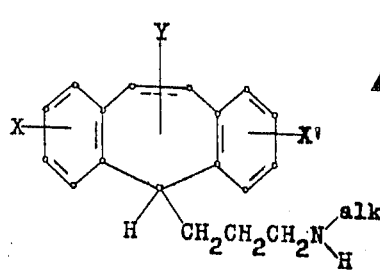

Method F (II) as a secondary amine

The tertiary amine is dissolved in a nonhydroxylic solvent such as benzene or ether and this solution is added slowly to a solution of cyanogen halide in the same solvent, while stirring and permitting the alkyl halide to escape. After the reaction is complete, the basic material is separated by washing with dilute acid and the cyanamide isolated by evaporating the solvent. The cyanamide is hydrolyzed to the secondary amine in an acidic or alkaline medium.

The 5-(3-dialkylaminopropylidene)-5H-dibenzo[a,d-]cycloheptenes and 5-(3-dialkylaminopropylidene)-10,11-dihydro-5H-dibenzo[a,d]cycloheptenes employed as starting compounds in method E may be prepared as described in Belgian Patents Nos. 578,122 and 584,061, respectively.

The 5-(3-dialkylaminopropylidene)-5H-dibenzo[a,d-]cycloheptenes and 5-(3-dialkylaminopropyl)-10,11-dihydro-5H-dibenzo[a,d]cycloheptenes may be prepared by condensing a 5-halo derivative of the selected 5H-dibenzo[a,d]cycloheptene with a dialkylaminopropyl Grignard reagent. This may be represented as follows:

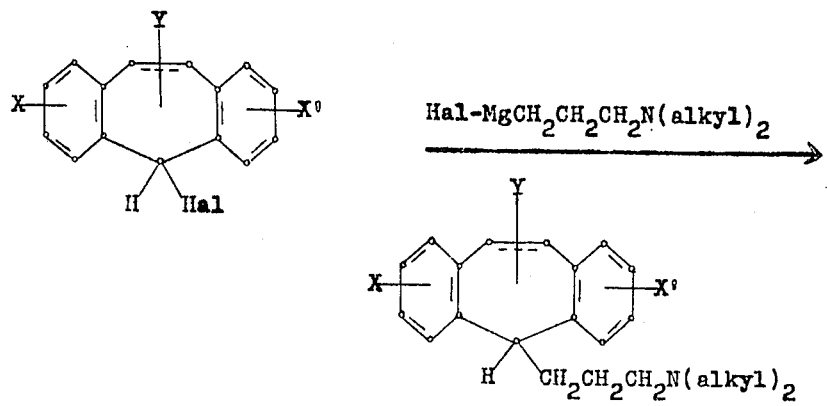

The starting compound, namely, the 5-halo-5H-dibenzo[a,d]cycloheptene or its 10,11-dihydro derivative, either of which may be further substituted by X and X' as defined above, may be made by using the process described by G. Berti in Gazz. Chim. Ital. 87, 293–309 (1957). The 5-halo-5H-dibenzo[a,d]cycloheptene or its 10,11-dihydro derivative having a bromine substituent in either the 10 or 11 position may be prepared in similar manner starting with the corresponding 5-keto compound which may be prepared as described hereinabove.

The Grignard reagent may be prepared by employing conventional procedures. The Grignard reagent may be prepared in a conventional solvent such as ether, tetrahydropyran, 2-methyltetrahydrofuran and tetrahydrofuran and the like, but tetrahydrofuran is preferred. These solvents may remain present during the reaction.

As the reaction is exothermic, the reactants should be combined very slowly or they may be combined more rapidly if external cooling is applied to the reaction vessel so as to maintain the temperature close to that of the room. When the addition is completed, heat is applied to maintain the temperature at up to refluxing temperature for from 15 to 60 minutes to obtain the maximum yield. The solvent can be removed by distilling it off under reduced pressure. The mixture is diluted with benzene and the excess Grignard reagent is hydrolyzed. As the desired end product is soluble in benzene, this layer is separated and the product isolated therefrom.

Further purification can be achieved by extraction with dilute acid which is then neutralized with alkali. The product is recovered therefrom with a solvent such as benzene or hexane which is then distilled off. The base of the product can be converted to a salt by the addition of such commonly used acids as hydrochloric acid, phosphoric acid, acetic acid, maleic acid and the like. To make the hydrochloride salt, it is preferable to add a solution of hydrogen chloride to a solution of the end product in dry alcohol.

A variation of method C to produce compounds II as the primary amines involves starting with the 5-halo (preferably chloro or bromo) drivatives of the selected 5H-dibenzo[a,d]cycloheptene. This method involves the following series of steps:

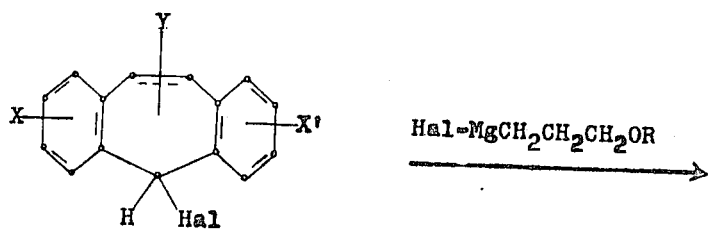

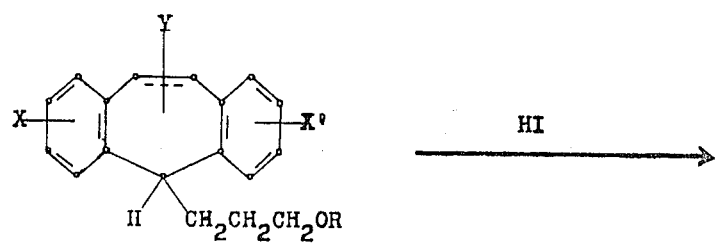

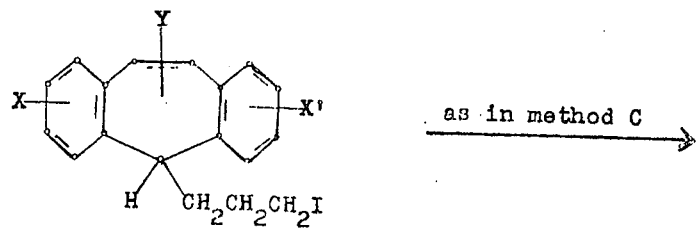

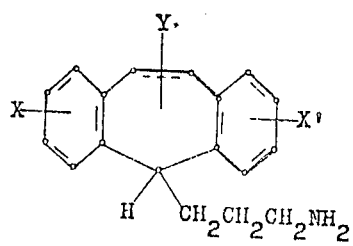

Method G

The R portion of the Grignard reagent is any radical such as a lower alkyl or aralkyl radical which will react with the hydriodic acid to result in replacement of the other group with the iodo radical. The resulting 5H-dibenzo[a,d]cycloheptene having an iodopropyl group at the 5-carbon atom is the same as the one in method C, and, as in mmethod C, may be converted to the primary amine of compounds II.

In method G, the reaction with the Grignard reagent may be carried out in the presence of a common solvent such as dry ether or tetrahydrofuran, the addition being slow to prevent a substantial temperature rise above room temperature. The usual procedures then are carried out. The primary amine of the end product of method G can be converted to a secondary amine by employing method B.

Still another method for producing the secondary amines of compounds II involves a catalytic debenzylation procedure. This may be represented as follows:

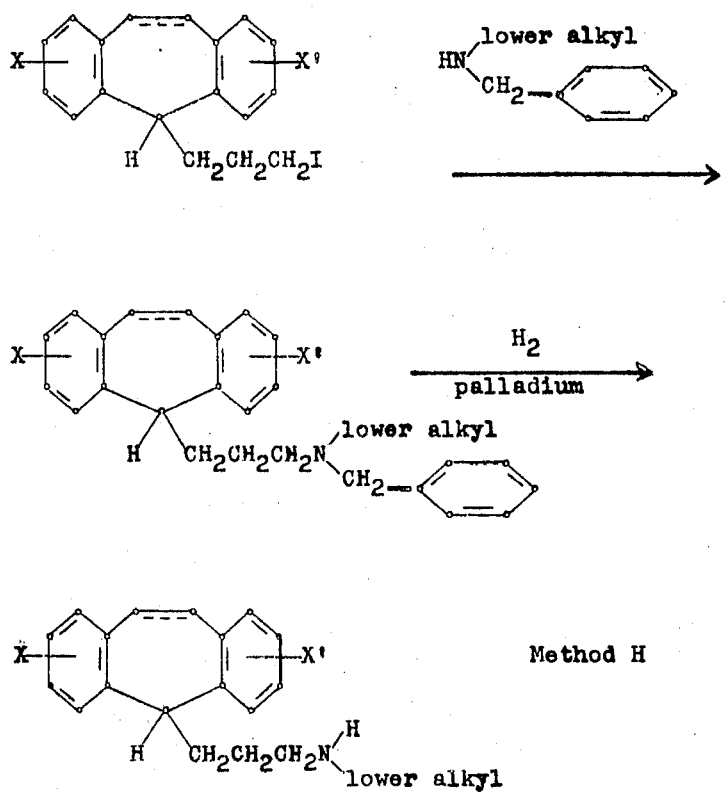

Method H

The starting compound of method H will be recognized as the iodo derivative produced by method C and method G. It is gradually combined with the N-alkylbenzylamine to prevent a substantial temperature rise above room temperature, a solvent such as absolute alcohol being used. Heat to a refluxing temperature should be applied for from 15 to 60 minutes and the solvent distilled off. The selective debenzylation action of hydrogen in the presence of palladium is utilized to remove the benzyl moiety and produce the secondary amine of compounds II. The alkyl radical of the N-alkylbenzylamine is selected to produce the radical R of compounds II.

The following examples are illustrative of the many compounds contemplated by the invention and falling within the scope of the claims.

EXAMPLE 1

5-(3-Aminopropylidene)-5H-dibenzo[a,d]cycloheptene

A. 5-Ethyl-5-hydroxy-5H-dibenzo[a,d]cycloheptene 5H-dibenzo[a,d]cyclohepten-5-one (15.5 g., 0.075 mole) is added in portions to a solution of ethylmagnesium bromide, prepared from 3.64 g. (0.15 mole) of magnesium and 16.4 g. of ethyl bromide in ether. After stirring for 1 hour at room temperature, the mixture is heated to refluxing for 15 minutes, then cooled, and the Grignard adduct is hydrolyzed by cautiously adding ammonium chloride solution. The crude 5-ethyl-5-hydroxy-5H-dibenzo[a,d]cycloheptene is recovered from the ether layer in a yield of 16.78 g. (95%), m.p., 63°–65° (clearing at 70°C.). After recrystallization from petroleum ether, hexane and finally isopropyl alcohol, an analytical sample melted at 63°–65°C.

Analysis, Calcd. for $C_{17}H_{16}O$: C, 86.40; H, 6.83. Found: C, 86.31; H, 6.50.

B. 5-Ethylidene-5H-dibenzo[a,d]cycloheptene

5-Ethyl-5-hydroxy-5H-dibenzo[a,d]cycloheptene (13.7 g., 0.058 mole) is dissolved in 80 ml. of acetyl chloride and the solution heated to refluxing for 90 minutes. The acetyl chloride is evaporated under reduced pressure and the residue dissolved in benzene.

After washing with alkali followed by a water wash, the benzene is removed and the product distilled under reduced pressure. The desired 5-ethylidene-5H-dibenzo[a,d]cycloheptene is obtained as the fraction boiling at 130°–135°C. (0.02 mm.). It crystallized on cooling. The compound was purified further by recrystallization from 95% alcohol.

C. 5-(2-Bromoethylidene)-5H-dibenzo[a,d]cycloheptene

A mixture of 5-ethylidene-5H-dibenzo[a,d]cycloheptene (10.9 g., 0.05 mole), N-bromosuccinimide (8.9 g., 0.05 mole), benzoyl peroxide (15 mg.) and 150 ml. of carbon tetrachloride is stirred and heated to refluxing on the steam-bath for 4 hours. After cooling, the succinimide is separated by filtration and washed with carbon tetrachloride. The combined filtrate and washings are evaporated to dryness under reduced pressure. Crystallization of the residual solid from petroleum ether gave 5-(2-bromoethylidene)-5H-dibenzo[a,d]cycloheptene in a yield of 10.65 g. (72%), m.p. 87.5°–89.5°C. An analytical sample, after recrystallization from petroleum ether, melted at 89°–90°C.

Analysis, Calcd. for $C_{17}H_{13}Br$: C, 68.70; H, 4.41; Br, 26.89. Found: C, 68.51; H, 4.38; Br, 26.76.

D. 5-(2-Cyanoethylidene)-5H-dibenzo[a,d]cycloheptene

A solution of 5-(2-bromoethylidene)-5H-dibenzo[a,d]cycloheptene (7.5 g., 0.025 mole) in 75 ml. of acetone is treated with a solution of potassium cyanide (5.0 g., 0.077 mole) in 15 ml. of water and the mixture heated to refluxing for 12 hours. The solution is evaporated to dryness under reduced pressure and the residue partitioned between ether and water. The ethereal layer is separated, washed with water, and dried over anhydrous sodium sulfate. Evaporation of the ether under reduced pressure gave an oily solid residue. Trituration with a mixture of petroleum ether - ether (3:1), 40 ml., afforded white crystals, m.p. 95°–101°C. The yield of 5-(2-cyanoethylidene)-5H-dibenzo[a,d]cycloheptene is 4.9 g. (81%). Repeated recrystallizations from isopropyl alcohol-water and from hexane gave an analytical sample melting at 103°–105°C.

Analysis, Calcd. for $C_{18}H_{13}N$: C, 88.86; H, 5,38; N, 5.76. Found: C, 88.95; H, 5.18; N, 5.74.

E. 5-(3-Aminopropylidene)-5H-dibenzo[a,d]cycloheptene

In a system protected by a drying tube and in which a nitrogen atmosphere is maintained, lithium aluminum hydride (380 mg., 0.01 mole) is suspended in 15 ml. of dry, peroxide-free tetrahydrofuran. The mixture is stirred and heated to refluxing for 4 hours. After cooling in an ice-bath, the mixture is stirred while a solution of 5-(2-cyanoethylidene)-5H-dibenzo[a,d]cycloheptene (1.21 g., 0.005 mole) in 20 ml. of tetrahydrofuran is added dropwise over 20 minutes. The deep red solution is stirred for 1 hour in the cold and then hydrolyzed by the successive dropwise addition of water, 0.4 ml., 20% sodium hydroxide, 0.4 ml., and water, 1.0 ml. The granular precipitate is filtered and washed with absolute ether. The combined filtrate and washings are evaporated to dryness under reduced pressure. The residual yellow oily base is dissolved in absolute alcohol and treated with a solution of maleic acid in absolute alcohol. Dilution with ether precipitates the hydrogen maleate as white crystals, m.p. 171°–173°C., dec. The yield of 5-(3-aminopropylidene)-5H-dibenzo[a,d]cycloheptene hydrogen maleate is 0.45 g. (25%). Repeated crystallizations from mixtures of absolute alcohol-absolute ether gave an analytical sample melting at 176.5°–177.5°C., dec.

Analysis, Calcd. for $C_{18}H_{17}N \cdot C_4H_4O_4$: C, 72.71; H, 5.83; N, 3.86. Found: C, 72.79; H, 6.00; N, 3.79.

EXAMPLE 2

5-(3-Ethylaminopropylidene)-5H-dibenzo[a,d]cycloheptene

A. 5-(3-Acetamidopropylidene)-5H-dibenzo[a,d]cycloheptene 5-(3-Aminopropylidene)-5H-dibenzo[a,d]cycloheptene is dissolved in acetic anhydride and the solution is heated to refluxing for 20 minutes. The solution is then cooled and poured into a large volume of water. The mixture is stirred until the excess acetic anhydride is hydrolyzed. The product is extracted into ether, the extract washed with sodium bicarbonate solution, followed by washing with water and dried over sodium sulfate. The product is isolated by evaporating the ether.

B. 5-(3-Ethylaminopropylidene)-5H-dibenzo[a,d]cycloheptene 5-(3-Acetamidopropylidene)-5H-dibenzo[a,d]cycloheptene is dissolved in absolute ether. The solution is added dropwise to a stirred solution of lithium aluminum hydride in ether, containing 1.25 molar equivalents of the hydride. The mixture is stirred for 2 hours at room temperature, then for 15 hours at reflux. The mixture is then cooled and stirred while water is added cautiously, followed by sodium hydroxide solution. The ether layer is separated, washed with water and dried over sodium sulfate. The product is obtained by evaporation of the ether and purified by vacuum distillation.

EXAMPLE 3

5-(3-Aminopropyl)-5H-dibenzo[a,d]cycloheptene

A. 5-(3-Ethoxypropyl)-5-hydroxy-5H-dibenzo[a,d]cycloheptene

The Grignard reagent is prepared from 12.55 g. (0.075 mole) of 3-ethoxypropyl bromide and 1.82 g. (0.075 mole) of magnesium in ether. The solution is cooled in an ice-bath and a solution of 5.15 g. (0.025 mole) of 5H-dibenzo[a,d]cyclohepten-5-one in dry ether is added dropwise with stirring. The mixture is stirred at room temperature for 2 hours, then at reflux for 30 minutes. The Grignard adduct then is decomposed by pouring the reaction mixture into a mixture of ice and ammonium chloride solution. The ether layer is separated and the aqueous layer extracted further with ether. Evaporation of the ether gives the product as an oily crystalline solid. Two recrystallizations from alcohol gave product, m.p. 129°–130°C.

Analysis, Calcd. for $C_{20}H_{22}O_2$: C, 81.60; H, 7.54. Found: C, 81.28; H, 7.50.

B. 5-(3-Iodopropyl)-5H-dibenzo[a,d]cycloheptene

A solution of 9.25 g. (0.0314 mole) of 5-(3-ethoxypropyl)-5-hydroxy-dibenzo[a,d]cycloheptene prepared as above in 45 ml. of acetic anhydride is heated on the steam-bath for 90 minutes then cooled to 65°C. A stream of nitrogen is passed through the solution while 30 ml. of hydriodic acid (sp. gr., 1.5) is added in portions, keeping the temperature below 90°C. The solution develops a dark brown iodine color during the addition. The solution is heated to 80°C. for 30 minutes, then cooled and poured into ice-water. The brown oil that separates is extracted into benzene and the extract washed with water, dilute sodium thiosulfate solution and finally with water. Evaporation of the benzene gives the product 5-(3-iodopropyl)-5H-dibenzo[a,d]cycloheptene as a yellow oil. A sample gives a precipitate with alcoholic silver nitrate solution.

C. 5-(3-Phthalimidopropyl)-5H-dibenzo[a,d]cycloheptene 5-(3-Iodopropyl)-5H-dibenzo[a,d]cycloheptene, 1.8 g. (0.005 mole), is dissolved in 10 ml. of dimethylformamide. The solution is stirred while 930 mg. (0.0051 mole) of potassium phthalimide is added. When the addition is complete, the mixture is heated to 85°–90°C. for 40 minutes, then cooled, diluted with chloroform and poured into water. The chloroform layer is separated and the aqueous layer extracted further with chloroform. Evaporation of the chloroform gives the product as an oily crystalline solid. Several recrystallizations from isopropyl alcohol gave product, m.p. 125.5°–131.5°C.

Analysis Calcd. for $C_{26}H_{21}O_2N$: C, 82.30; H, 5.58; N, 3.69. Found: C, 82.46; H, 5.60; N, 3.70.

D. 5-(3-Aminopropyl)-5H-dibenzo[a,d]cycloheptene 5-(3-Phthalimidopropyl)-5H-dibenzo[a,d]cycloheptene, 2.15 g. (0.0054 mole), is dissolved in 50 ml. of hot 95% ethanol. Hydrazine hydrate, 0.6 ml., is added and the solution heated to refluxing for 2 hours. The solution then is cooled, acidified, and the precipitate of phthalhydrazide removed by filtration. Ethanol is distilled from the filtrate under reduced pressure and the residue dissolved in 40 ml. of water. The filtered solution is evaporated by heating under reduced pressure to a volume of approximately 20 ml. Upon cooling, the hydrochloride salt of 5-(3-aminopropyl)-5H-dibenzo[a,d]cycloheptene is precipitated in a yield of 1.35 g. (87.5%). After recrystallization from a mixture of ethanol and ether and from isopropyl alcohol, an analytical sample melted at 263°–265°C., dec.

Analysis, Calcd. for $C_{18}H_{19}N \cdot HCl$: C, 75.64; H, 7.05; N, 4.90. Found: C, 75.54; H, 6.77; N, 4.78.

EXAMPLE 4

5-(3-n-Butylaminopropyl)-5H-dibenzo[a,d]cycloheptene

A. 5-(3-Butyramidopropyl)-5H-dibenzo[a,d]cycloheptene

A solution of 5-(3-aminopropyl)-5H-dibenzo[a,d]cycloheptene (0.75 g., 0.003 mole) in 5 ml. of dry pyridine is treated with 0.7 ml. of butyric anhydride and then heated to refluxing for 30 minutes. The cooled solution is poured into 50 ml. of water and the mixture allowed to stand at room temperature overnight. The oil is extracted into benzene and the benzene extract washed with water, 3N hydrochloric acid, and water. Distillation of the benzene under reduced pressure gave an oily residue which solidified on standing. Trituration with petroleum ether afforded 5-(3-butyramidopropyl)-5H-dibenzo[a,d]cycloheptene as a white crystalline solid, m.p. 76°–80°C., in a yield of 0.80 g. (83%).

B. 5-(3-n-Butylaminopropyl)-5H-dibenzo[a,d]cycloheptene

In a system protected by a drying tube and in which a nitrogen atmosphere is maintained, a solution of the product from Step A. (0.80 g., 0.0075 mole) in 25 ml. of absolute ether is added dropwise to a stirred suspension of lithium aluminum hydride (0.19 g., 0.0025 mole) in 15 ml. of absolute ether. After stirring at reflux for 1 hour, the mixture is cooled in ice and hydrolyzed by the successive dropwise addition of water, 0.2 ml., 20% sodium hydroxide, 0.2 ml., and water, 0.6 ml.

The granular precipitate is collected and washed thoroughly with ether. The combined ethereal filtrate and washings are washed with water, dried over anhydrous sodium sulfate, and evaporated to dryness. The residual oily base is dissolved in absolute ether and treated with a solution of maleic acid (10% excess) in absolute alcohol. The 5-(3-n-butylaminopropyl)-5H-dibenzo[a,d]cycloheptene hydrogen maleate is obtained by dilution of the solution with absolute ether as white needles, m.p. 102°–107°C., in a yield of 0.65 g. (60%). Recrystallization from mixtures of isopropyl alcohol - absolute ether and absolute alcohol - absolute ether gives product, m.p. 107.5°–109°C.

Analysis, Calcd. for $C_{22}H_{27}N \cdot C_4H_4O_4$: C, 74.08; H, 7.41; N, 3.32. Found: C, 73.74; H, 7.38; N, 3.27.

EXAMPLE 5

5-(3-Isopropylaminopropyl)-5H-dibenzo[a,d]cycloheptene

A suspension of platinum oxide (20 mg.) in 2 ml. of absolute alcohol is pre-reduced by shaking with hydrogen in a Hershberg apparatus. A solution of 5-(3-aminopropyl)-5H-dibenzo[a,d]cycloheptene (0.75 g., 0.003 mole) and acetone (0.5 ml.) in 5 ml. of absolute alcohol is added and the mixture shaken with hydrogen in a Hershberg apparatus until the hydrogen uptake is complete. Catalyst is filtered through a mat of diatomaceous earth and washed with absolute alcohol. The combined filtrate and washings are evaporated to dryness on the steam-bath under reduced pressure. The residual oily base is dissolved in absolute alcohol and treated with a solution of dry hydrogen chloride in absolute alcohol. The white crystalline 5-(3-isopropylaminopropyl)-5H-dibenzo[a,d]cycloheptene hydrochloride is precipitated by addition of absolute ether in a yield of 0.80 g. (92%), m.p. 234°–236°C. The melting point was unchanged by a further recrystallization from a mixture of isopropyl alcohol and absolute ether.

Analysis, Calcd. for $C_{21}H_{25}N \cdot HCl$: C, 76.92; H, 7.99; N, 4.27. Found: C, 76.98; H, 7.78; N, 4.27.

EXAMPLE 6

5-(3-Methylaminopropylidene)-5H-dibenzo[a,d]cycloheptene

A. 5-[3-(N-Cyano-N-methyl)aminopropylidene]-5H-dibenzo[a,d]cycloheptene

A solution of 23.06 g. (0.0834 mole) of 5-(3-dimethylaminopropylidene)-5H-dibenzo[a,d]cycloheptene in 61 ml. of benzene is added dropwise to a stirred solution of 9.80 g. (0.0917 mole) of cyanogen bromide in 38 ml. of benzene. Some heat is evolved. The mixture is stirred for 3 hours at room temperature, and filtered to remove any precipitate which forms. The filtrate, together with a benzene wash of the precipitate, is evaporated to dryness on a steam-bath under reduced pressure to remove excess cyanogen bromide and solvent. The residual crude cyanamide is dissolved in benzene, and the solution is washed with dilute hydrochloric acid to remove any unchanged amine, then with water. The benzene solution is then evaporated under reduced pressure leaving 5-[3-(N-cyano-N-methyl)aminopropylidene]-5H-dibenzo[a,d]cycloheptene as a yellow oil weighing typically 19.6 g.

B. 5-(3-Methylaminopropylidene)-5H-dibenzo[a,d]cycloheptene

The oily cyanamide (19.6 g.) prepared as in A above together with 500 ml. of glacial acetic acid, 330 ml. of water, and 50 ml. of concentrated hydrochloric acid is heated under reflux for 16 hours, thereby effecting hydrolysis and decarboxylation and forming the product. The reaction mixture is concentrated to a small volume by heating under reduced pressure and the residue is dissolved in 250 ml. of water containing 1 ml. of concentrated hydrochloric acid. The aqueous solution is washed with benzene, and rendered alkaline by the addition of excess potassium carbonate. The free base thus liberated is extracted into ether and the ether solution dried over anhydrous potassium carbonate. Evaporation of the ether under reduced pressure on the steam-bath leaves a residue of 5-(3-methylaminopropylidene)-5H-dibenzo[a,d]cycloheptene, as an oil.

The free base may be converted to the oxalate by dissolution in warm absolute ethanol, addition of an equimolar quantity of oxalic acid dissolved in ethanol, and precipitation by the addition of ether. After recrystallization from a mixture of methanol and ethyl acetate, the thus-formed hydrogen oxalate salt melts at about 202.5°–203.5°C.

Analysis, Calcd. for $C_{19}H_{19}N.C_2H_2O_4$: C, 71.78; H, 6.02; N, 3.99. Found: C, 71.95; H, 6.00; N, 3.95.

Alternatively, the cyanamide can be hydrolyzed under alkaline conditions as follows:

The cyanamide, obtained as described in Step A. (2.0 g., 0.007 mole) is mixed with a hot solution of 25 g. of potassium hydroxide in 38 ml. of absolute methanol. The mixture is heated to refluxing with stirring for 45 hours. The reaction mixture then is diluted with water and the yellow oil that separates is extracted into benzene. After washing with water and drying over sodium sulfate, the benzene is evaporated to give 1.75 g. of a yellow oily residue. The basic material is extracted into 1N hydrochloric acid and after separating the neutral material by extracting with ether, the basic material is recovered by making the aqueous layer basic and extracting with ether. Evaporation of the ether gives 1.46 g. of the base, 5-(3-methylaminopropylidene)-5H-dibenzo[a,d]cycloheptene. Conversion to the oxalate is carried out as described above.

The hydrochloride salt may be formed directly from the crude free base or through the oxalate as follows: An aqueous solution of the oxalate salt is basified with lithium hydroxide and the free base extracted into benzene. Evaporation of the benzene leaves the base in substantially pure form. Treatment of the base with ethanolic hydrogen chloride and precipitation by the addition of ether gives the hydrochloride salt which, after recrystallization from a mixture of ethanol and ether, melts at 180°–182°C.

Analysis, Calcd. for $C_{19}H_{19}N.HCl$: C, 76.61; H, 6.77; N, 4.70; Cl, 11.91 Found: C, 76.93; H, 6.89; N, 4.65; Cl, 11.85.

EXAMPLE 7

5-(3-Methylaminopropylidene)-10,11-dihydro-5H-dibenzo-[a,d]cycloheptene

Upon following the procedure given in Example 6 A, but employing an equivalent quantity of 5-(3-dimethylaminopropylidene)-10,11-dihydro-5H-dibenzo[a,d]cycloheptene in place of 5-(3-dimethylaminopropylidene)-5H-dibenzo[a,d]cycloheptene, the corresponding cyanamide is obtained. Upon hydrolysis, according to the procedure of Example 6 B, there is obtained 5-(3-methylaminopropylidene)-10,11-dihydro-5-H-dibenzo[a,d]cycloheptene. This may be converted to its hydrochloride salt directly by treatment with ethanolic hydrogen chloride as described in Example 6 B. After recrystallization from a mixture of alcohol and ether, the hydrochloride salt melts at about 215.7°–216.7°C.

Analysis, Calcd. for $C_{19}H_{21}N.HCl$: C, 76.10; H, 7.40; N, 4.67. Found: C, 76.08; H, 7.30; N, 4.54.

EXAMPLE 8

5-(3-Methylaminopropyl)-5H-dibenzo[a,d]cycloheptene

Upon following the procedure given in Example 6 A., but employing an equivalent quantity of 5-(3-dimethylaminopropyl)-5H-dibenzo[a,d]cycloheptene in place of 5-(3-dimethylaminopropylidene)-5-H-dibenzo[a,d]cycloheptene, the corresponding cyanamide is obtained. Upon hydrolysis, according to the procedure of Example 6 B, there is obtained 5-(3-methylaminopropyl)-5H-dibenzo[a,d]cycloheptene. This may be converted to its hydrochloride salt directly by treatment with ethanolic hydrogen chloride as described in Example 6 B. After recrystallization from a mixture of isopropyl alcohol and ether, the hydrochloride salt melts at 166.5°–167.5°C. (uncorrected).

Analysis, Calcd. for $C_{19}H_{21}N.HCl$: C, 76.11; H, 7.40; N, 4.67. Found: C, 76.14; H, 7.30; N, 4.64.

EXAMPLE 9

5-(3-Dimethylaminopropyl)-5H-dibenzo[a,d]cycloheptene hydrochloride

A. 3-Dimethylaminopropylmagnesium chloride

Magnesium turnings (1.08 g., 0.0442 g. atom) are placed in a 200 ml. 3-necked flask equipped with a stirrer, a dropping funnel and a reflux condenser carrying a drying tube. An atmosphere of dry nitrogen is maintained in the apparatus throughout the reaction. A crystal of iodine is added followed by 10 ml. of dry tetrahydrofuran. A 3 ml. portion of 3-dimethylaminopropylmagnesium chloride solution from a previous experiment is added and the mixture heated to refluxing on the steam-bath. A solution of 3-dimethylaminopropyl chloride (5.37 g., 0.0442 mole) in 35 ml. of dry tetrahydrofuran is added dropwise, refluxing being maintained by the application of heat when necessary. When the addition is complete, the mixture is refluxed for 2 hours when almost all of the magnesium is dissolved.

Instead of using 3-dimethylaminopropylmagnesium chloride to initiate the reaction, ethyl bromide can be employed in a quantity of 0.05 mole per mole of magnesium.

B. 5-(3-Dimethylaminopropyl)-5H-dibenzo[a,d]cycloheptene hydrochloride

The Grignard solution prepared in Step A. is cooled to room temperature and stirred while a solution of 5.05 g. (0.0221 mole) of 5-chloro-5H-dibenzo[a,d]cycloheptene in 25 ml. of dry tetrahydrofuran is added dropwise, external cooling being applied as required to maintain the temperature close to room temperature. When the addition is complete, the mixture is heated to refluxing for 15 minutes. The bulk of the tetrahydrofuran then is distilled under reduced pressure, keeping the water-bath temperature at 50°–60°C. The syrupy mixture is dissolved in 75 ml. of benzene and water, 15 ml., is added dropwise with stirring. The benzene layer is decanted from the gelatinous precipitate which then is re-extracted with three 20 ml. portions of boiling benzene. The combined benzene extracts are washed with water and extracted with three 15 ml. portions of 3N hydrochloric acid. The acid extract is made basic with sodium hydroxide and the yellow oily base that separates is extracted into hexane. After washing the combined extracts with water, the hexane is evaporated and the product obtained as a yellow oil in a yield of 4.61 g. The base is converted to the hydrochloride by dissolving it in a mixture of 15 ml. of absolute alcohol and 15 ml. of absolute ether and adding 1.8 ml. of a 10.28 N solution of dry hydrogen chloride in absolute alcohol. The solution then is diluted to incipient crystallization by the addition of 25 ml. of absolute ether. The yield of 5-(3-dimethylaminopropyl)-5H-dibenzo[a,d]cycloheptene hydrochloride, m.p. 186°–190°C. is 4.17 g. Recrystallization from mixtures of absolute alcohol and absolute ether gives the product, m.p. 191°–193°C.

Analysis, Calcd. for $C_{20}H_{23}N.HCl$: C, 76.53; H, 7.71; N, 4.46. Found: C, 76.23; H, 7.83; N, 4.45.

EXAMPLE 10

10,11-Dihydro-5-(3-methylaminopropyl)-5H-dibenzo[a,d]cycloheptene 10,11-Dihydro-5-(3-dimethylaminopropyl)-5H-dibenzo[a,d]cycloheptene is converted to the corresponding cyanamide by following the procedure of Example 6A. The cyanamide (5.03 g.) together with 60 ml. of glacial acetic acid, 40 ml. of water and 8 ml. of concentrated hydrochloric acid is heated to refluxing for 16 hours. The reaction mixture is evaporated to dryness by heating under reduced pressure. Crystallization of the residual solid from isopropyl alcohol gives 4.48 g. (86%) of the hydrochloride salt of 10,11-dihydro-5-(3-methylaminopropyl)-5H-dibenzo[a,d]cycloheptene melting at 174°–175°C.

Analysis, Calcd. for $C_{19}H_{23}N.HCl$: C, 75.60; H, 8.01; N, 4.64. Found: C, 75.89; H, 8.05; N, 4.61.

The starting 10,11-dihydro-5-(3-dimethylaminopropyl)-5H-dibenzo[a,d]cycloheptene used in this example may be prepared by following Steps A and B in Example 9, but employing 5-chloro-10,11-dihydro-5H-dibenzo[a,d]cycloheptene as the starting compound.

EXAMPLE 11

3-Chloro-10,11-dihydro-5-(3-methylaminopropyl)-5H-dibenzo[a,d]cycloheptene

3-Chloro-10,11-dihydro-5-(3-dimethylaminopropyl)-5H-dibenzo[a,d]cycloheptene is converted to the corresponding cyanamide by following the procedure of Example 6 A. Upon hydrolysis, according to the procedure of Example 6 B, there is obtained 3-chloro-10,11-dihydro-5-(3-methylaminopropyl)-5H-dibenzo[a,d]cycloheptene. This may be converted to its hydrochloride salt directly by treatment with ethanolic hydrogen chloride as described in Example 6 B. After recrystallization from a mixture of isopropyl alcohol and ether, the hydrochloride salt melts at 192.5°–193.5°C., dec.

Analysis, Calcd. for $C_{19}H_{22}NCl.HCl$: C, 67.85; H, 6.89; N, 4.17. Found: C, 68.09; H, 6.94; N, 4.13.

The starting 3-chloro-10,11-dihydro-5-(3-dimethylaminopropyl)-5H-dibenzo[a,d]cycloheptene used in this example may be prepared by following Steps A and B of the above Example 9, employing 3,5-dichloro-10,11-dihydro-5H-dibenzo[a,d]cycloheptene as the starting compound.

EXAMPLE 12

5-(3-Aminopropyl)-5H-dibenzo[a,d]cycloheptene

A. 5-(3-Ethoxypropyl)-5H-dibenzo[a,d]cycloheptene

The Grignard reagent is prepared from 6.44 g. (0.0386 mole) of 3-ethoxypropyl bromide and 940 mg. (0.0386 g. atom) of magnesium in ether. A solution of 5.67 g. (0.025 mole) of 5-chloro-5H-dibenzo[a,d]cycloheptene in a mixture of dry ether and tetrahydrofuran is added dropwise with stirring. The mixture is stirred at room temperature for 1 hour. The Grignard adduct then is decomposed by pouring the reaction mixture into a mixture of ice and ammonium chloride solution. The ether layer is separated, the aqueous layer extracted further with ether. Evaporation of the ether and distillation of the residue under reduced pressure gives the product as a yellow oil, b.p. 145°–148°C. (0.1 mm.)

Analysis, Calcd. for $C_{20}H_{22}O$: C, 86.28; H, 7.97. Found: C, 86.84; H, 7.97.

B. 5-(3-Iodopropyl)-5H-dibenzo[a,d]cycloheptene

This product is obtained by following the procedure of Example 3 B, but starting with 5-(3-ethoxypropyl)-5H-dibenzo[a,d]cycloheptene. To obtain as the end product the compound of the title, the remaining procedure of Example 3 is followed.

EXAMPLE 13

3-Chloro-5-(3-aminopropyl)-5H-dibenzo[a,d]cycloheptene

A. 3-Chloro-5-(3-ethoxypropyl)-5H-dibenzo[a,d]cycloheptene 3,5-Dichloro-5H-dibenzo[a,d]cycloheptene, dissolved in absolute ether, is added dropwise with stirring to a solution containing one equivalent of 3-ethoxypropylmagnesium bromide in ether. The mixture is stirred at room temperature for 1 hour, then at reflux for 2 hours. The mixture then is cooled, treated with dilute hydrochloric acid and the ether separated, washed with water and dried. The product is isolated by evaporation of the ether.

B. 3-Chloro-5-(3-iodopropyl)-5H-dibenzo[a,d]cycloheptene

3-Chloro-5-(3-ethoxypropyl)-5H-dibenzo[a,d]cycloheptene (0.03 mole) is dissolved in 45 ml. of acetic anhydride. The solution is heated to 65°C. and nitrogen is passed through while 30 ml. of hydriodic acid (sp. gr., 1.5) is added gradually, keeping the temperature below 90°C. The solution is heated to approximately 80°C. for 30 minutes, then cooled and poured into ice-water. The product is extracted into ether, the extract washed with dilute sodium thiosulfate solution, followed by dilute sodium bicarbonate solution and finally with water. The product is isolated by evaporation of the ether.

C. 3-Chloro-5-(3-phthalimidopropyl)-5H-dibenzo[a,d]cycloheptene

3-Chloro-5-(3-iodopropyl)-5H-dibenzo[a,d]cycloheptene is converted to 3-chloro-5-(3-phthalimidopropyl)-5H-dibenzo[a,d]cycloheptene by following the procedure of Example 3, Step C.

D. 3-Chloro-5-(3-aminopropyl)-5H-dibenzo[a,d]cycloheptene

3-Chloro-5-(3-phthalimidopropyl)-5H-dibenzo[a,d]cycloheptene is converted to 3-chloro-5-(3-aminopropyl)-5H-dibenzo[a,d]cycloheptene by following the procedure of Example 3, Step D.

EXAMPLE 14

3-Chloro-5-(3-ethylaminopropyl)-5H-dibenzo[a,d]cycloheptene

A. 3-Chloro-5-(3-acetamidopropyl)-5H-dibenzo[a,d]cycloheptene

3-Chloro-5-(3-aminopropyl)-5H-dibenzo[a,d]cycloheptene is dissolved in acetic anhydride and the solution heated to refluxing for 20 minutes. The solution then is cooled and poured into a large volume of water. The mixture is stirred until the excess reagent is hydrolyzed. The product then is extracted into ether, the extract washed with sodium bicarbonate solution, followed by washing with water and dried over sodium sulfate. The product is isolated by evaporating the ether.

B. 3-Chloro-5-(3-ethylaminopropyl)-5H-dibenzo[a,d]cycloheptene

3-Chloro-5-(3-acetamidopropyl)-5H-dibenzo[a,d]cycloheptene is dissolved in absolute ether. The solution is added dropwise to a stirred solution of lithium aluminum hydride in ether, containing 1.25 molar equivalents of the hydride. The mixture is stirred for 2 hours at room temperature, then for 15 hours at reflux. The mixture then is cooled and stirred while water is added cautiously followed by sodium hydroxide solution. The ether layer is separated, washed with water and dried over sodium sulfate. The product is obtained by evaporation of the ether and purified by vacuum distillation.

EXAMPLE 15

5-(3-Ethylaminopropyl)-5H-dibenzo[a,d]cycloheptene

A. 5-[3-(N-Benzyl-N-ethylamino)-propyl]-5H-dibenzo[a,d]cycloheptene 5-(3-Iodopropyl)-5H-dibenzo[a,d]cycloheptene is added gradually to an excess of N-ethyl benzylamine in absolute alcohol with stirring and cooling. The reaction mixture then is heated to refluxing for 30 minutes and the alcohol distilled under reduced pressure. The residue is warmed with dilute acid and the acid-insoluble material separated. The aqueous layer then is rendered alkaline with sodium hydroxide and the liberated bases extracted into ether. The ether is evaporated and the product isolated by vacuum distillation.

B. 5-(3-Ethylaminopropyl)-5H-dibenzo[a,d]cycloheptene

5-[3-(N-Benzyl-N-ethylamino)-propyl]-5H-dibenzo[a,d]cycloheptene is dissolved in absolute alcohol and hydrogenated over palladium on alumina catalyst at 40°–60°C. The catalyst is separated and the product isolated by evaporating the solvent.

EXAMPLE 16

5-(3-Ethylaminopropyl)-5H-dibenzo[a,d]cycloheptene

A. 5-(3-Acetamidopropyl)-5H-dibenzo[a,d]cycloheptene

A solution of 5-(3-aminopropyl)-5H-dibenzo[a,d]cycloheptene (0.75 g., 0.003 mole) in 5 ml. of dry pyridine is treated with 1 ml. of acetic anhydride and then heated to refluxing for 30 minutes. The cooled solution is poured into 100 ml. of water and the oil extracted into benzene. The benzene extract is washed with water, 3N hydrochloric acid, water, and evaporated to dryness under reduced pressure. The 5-(3-acetamidopropyl)-5H-dibenzo[a,d]cycloheptene is obtained as a yellow oily residue weighing 0.87 g.

B. 5-(3-Ethylaminopropyl)-5H-dibenzo[a,d]cycloheptene

In a system protected by a drying tube and in which a nitrogen atmosphere is maintained, a solution of the product from Step A (0.87 g., 0.003 mole) in 25 ml. of absolute ether is added dropwise over a period of 30 minutes to a stirred solution of lithium aluminum hydride (0.25 g., 0.0066 mole) in 15 ml. of absolute ether. After stirring at reflux for 6 hours, the mixture is allowed to stand at room temperature overnight. The mixture is cooled in ice and stirred while water, 0.25 ml., 20% sodium hydroxide, 0.25 ml., and water, 0.75 ml., are added cautiously dropwise in succession. The granular precipitate is collected and washed thoroughly with ether. The combined ethereal filtrate and washings are washed with water and dried over anhydrous sodium sulfate. Ether is evaporated under reduced pressure to obtain the oily base. The hydrochloride is prepared by treating a solution of the base in absolute alcohol - absolute ether with a solution of dry hydrogen chloride in absolute alcohol. The white crystalline 5-(3-ethylaminopropyl)-5H-dibenzo-[a,d]cycloheptane hydrochloride is obtained by dilution of the solution with absolute ether in a yield of 0.50 g. (53%), m.p. 224.5°–226.5°C., dec. Repeated recrystallizations from absolute alcohol - absolute ether and isopropyl alcohol - absolute ether mixtures raised the m.p. to 227.5°–228.5°C., dec.

Analysis, Calcd. for $C_{20}H_{23}N \cdot HCl$: C, 76.53; H, 7.71; N, 4.46.

Found: C, 76.28; H, 7.68; N, 4.42.

EXAMPLE 17

3-Chloro-5-(3-methylaminopropyl)-5H-dibenzo[a,d]cycloheptene

A. 3-Chloro-5-(3-dimethylaminopropyl)-5H-dibenzo[a,d]cycloheptene

3-Dimethylaminopropylmagnesium chloride is prepared from magnesium turnings (1.22 g., 0.051 g. atom) and 3-dimethylaminopropyl chloride (6.2 g., 0.051 mole) in 25 ml. of tetrahydrofuran following the method of Example 9, Step A. In a nitrogen atmosphere, a solution of 3,5-dichloro-5H-dibenzo[a,d]cycloheptene (6.65 g., 0.0255 mole) in 40 ml. of tetrahydrofuran is added dropwise to the stirred solution of the Grignard reagent while cooling in an ice-bath. The mixture is allowed to come to room temperature and stirred for 2 hours. The bulk of the solvent then is distilled below 50°C. under reduced pressure. The residue is dissolved in 50 ml. of benzene and water, 20 ml., is added dropwise with stirring and cooling. The benzene layer is decanted from the gelatinous precipitate which then is re-extracted with three 20 ml. portions of boiling benzene. The combined benzene extracts are washed with water and extracted with three 50 ml. portions of 1N hydrochloric acid. The acid extract is made basic with sodium hydroxide and the oily base that separates is extracted into hexane. After washing the combined extracts with water and drying over anhydrous sodium sulfate, the hexane is evaporated and the product obtained as a yellow oil in a yield of 6.13 g. The base is converted to the hydrogen maleate by dissolving it in 25 ml. of isopropyl alcohol and adding a solution of 2.5 g. of maleic acid in 10 ml. of isopropyl alcohol. Dilution to incipient crystallization with 50 ml. of absolute ether precipitates 3-chloro-5-(3-dimethylaminopropyl)-5H-dibenzo[a,d]cycloheptene hydrogen maleate, m.p. 144°–149°C. in a yield of 5.9 g. Recrystallization from mixtures of absolute alcohol - absolute ether and isopropyl alcohol - absolute ether gives the product, m.p. 153°–155°C.

Analysis, Calcd. for $C_{20}H_{22}NCl \cdot C_4H_4O_4$: C, 67.37; H, 6.13; N, 3.27.

Found: C, 67.54; H, 6.22; N, 3.21.

B. 3-Chloro-5-(3-N-cyano-N-methylaminopropyl)-5H-dibenzo[a,d]cycloheptene

In a system protected by a drying tube and in which a nitrogen atmosphere is maintained, a solution of 3-chloro-5-(3-dimethylaminopropyl)-5H-dibenzo[a,d]cycloheptene (0.78 g., 0.0025 mole) in 5 ml. of benzene is added dropwise to a stirred solution of cyanogen bromide, 0.7 ml. of a 4.25M solution in benzene, in 4.3 ml. of benzene. Stirring is continued for 1½ hours and the mixture then allowed to stand at room temperature overnight. Solvent and excess cyanogen bromide are evaporated under reduced pressure and the residue dissolved in benzene. The solution is washed with dilute hydrochloric acid, then with water, and evaporated to dryness under reduced pressure. The 3-chloro-5-(3-N-cyano-N-methylaminopropyl)-5H-dibenzo[a,d]cycloheptene is obtained as a yellow oily residue weighing 0.77 g. (95.5%).

C. 3-Chloro-5-(3-methylaminopropyl)-5H-dibenzo[a,d]cycloheptene

The oily cyanamide (0.77 g.) prepared as in B. above, is hydrolyzed according to the procedure of Example 6 B. There is obtained 3-chloro-5-(3-methylaminopropyl)-5H-dibenzo[a,d]cycloheptene as an oil weighing 0.60 g. This may be converted to its hydrochloride salt directly by treatment with ethanolic hydrogen chloride as described in Example 6 B. After recrystallization from mixtures of isopropyl alcohol - absolute ether and absolute methanol - acetone, the white crystalline hydrochloride melts at 193°–195°C., dec.

Analysis, Calcd. for $C_{19}H_{20}NCl \cdot HCl$: C, 68.26; H, 6.33; N, 4.19.

Found: C, 67.89; H, 6.39; N, 4.10.

EXAMPLE 18

3-Dimethylsulfamoyl-5-(3-methylaminopropyl)-5H-dibenzo[a,d]cycloheptene

A. 3-Bromo-7-fluorosulfonyl-10,11-dihydro-5H-dibenzo[a,d]cyclohepten-5-one

Fluorosulfonic acid, 100 ml., is placed in a 300 ml. 3-necked round bottom flask equipped with polyethylene inlet tube and polyethylene exit tube with drying tube half-filled with anhydrous sodium fluoride. A nitrogen atmosphere is maintained throughout the reaction. With stirring, 17.0 g. (0.059 mole) of 3-bromo-10,11-dihydro-5H-dibenzo[a,d]cyclohepten-5-one is added in portions over 20 minutes. After stirring another 10 minutes, the dark green solution is heated on the steam-bath for 6½ hours. The mixture then is cooled to room temperature, poured cautiously with stirring into 1.5 kg. of crushed ice, and allowed to stand overnight at room temperature. The brown solid is collected, washed with water, dried in a vacuum desiccator over sodium hydroxide, and then extracted in a Sohxlet extractor with 700 ml. of boiling cyclohexane for 16 hours. On cooling, the cyclohexane extract deposits 11.65 g. (53%) of 3-bromo-7-fluorosulfonyl-10,11-dihydro-5H-dibenzo[a,d]cyclohepten-5-one as dark yellow flakes, m.p. 148°–151°C. Recrystallizations from ether and cyclohexane give an analytical sample, m.p. 150°–152°C.

Analysis, Calcd. for $C_{15}H_{10}O_3FBrS$: C, 48.79; H, 2.73; S, 8.69.

Found: C, 48.78; H, 2.83; S, 8.87.

B. 3-Bromo-7-dimethylsulfamoyl-10,11-dihydro-5H-dibenzo[a,d]cyclohepten-5-one

3-Bromo-7-fluorosulfonyl-10,11-dihydro-5H-dibenzo[a,d]cyclohepten-5-one (2.5 g., 0.00677 mole) together with 30 ml. of 25% aqueous dimethylamine and 30 ml. of p-dioxane is heated to refluxing for 3 hours. The brown solution is evaporated to dryness under reduced pressure and the residue partitioned between benzene and water. After washing with water, the benzene layer is evaporated to dryness under reduced pressure, leaving 3-bromo-7-dimethylsulfamoyl-10,11-dihydro-5H-dibenzo[a,d]cyclohepten-5-one as a tan solid, m.p. 142°–145°C., in a yield of 2.1 g. (80%). An analytical sample melts at 146°–148°C. after crystallizations from mixtures of benzene and hexane and from methanol.

Analysis, Calcd. for $C_{17}H_{16}O_3NBrS$: C, 51.78; H, 4.09; N, 3.55.

Found: C, 51.71; H, 4.12; N, 3.53.

C. 3-Dimethylsulfamoyl-10,11-dihydro-5H-dibenzo[a,d]cyclohepten-5-one

3-Bromo-7-dimethylsulfamoyl-10,11-dihydro-5H-dibenzo[a,d]cyclohepten-5-one, 8.0 g. (0.0203 mole), is dissolved in a mixture of 100 ml. of absolute ethanol, 70 ml. of dimethylformamide, and 5 ml. of triethylamine. The solution is hydrogenated at atmospheric pressure and in the presence of 600 mg. of 10% palladium on charcoal catalyst until hydrogen uptake is complete. Catalyst is removed by filtration and washed with absolute ethanol. The filtrate is evaporated to dryness under reduced pressure and the residue triturated with benzene. The insoluble triethylamine hydrobromide is filtered and the benzene filtrate evaporated to dryness under reduced pressure. Crystallization of the residual white solid from absolute ethanol affords 6.1 g. (97%) of 3-dimethylsulfamoyl-10,11-dihydro-5H-dibenzo[a,d]cyclohepten-5-one, m.p. 122°–124°C. The melting point is unchanged after crystallization from absolute ethanol.

Analysis, Calcd. for $C_{17}H_{17}O_3NS$: C, 64.74; H, 5.44; N, 4.44.

Found: C, 64.20; H, 5.47; N, 4.16.

D. 3-Dimethylsulfamoyl-5H-dibenzo[a,d]cyclohepten-5-one

A mixture of 3-dimethylsulfamoyl-10,11-dihydro-5H-dibenzo[a,d]cyclohepten-5-one (6.1 g., 0.0194 mole), N-bromosuccinimide (3.6 g., 0.029 mole), benzoyl peroxide (50 mg.) and 50 ml. of benzene is stirred and heated to refluxing for 3 hours. The precipitated succinimide is filtered and washed with warm benzene. After washing with 5% aqueous sodium hydroxide and then with water, the benzene filtrate is evaporated to dryness under reduced pressure. The residual oily solid is suspended in 75 ml. of triethylamine and the mixture stirred at reflux for 16 hours. Triethylamine is evaporated under reduced pressure and the residual solid partitioned between benzene and water. The benzene layer is separated, washed with 3N hydrochloric acid and then with water, and evaporated to dryness under reduced pressure. Crystallization of the residual solid from 95% ethanol gives 2.83 g. (46.5%) of 3-dimethylsulfamoyl-5H-dibenzo[a,d]cyclohepten-5-one, m.p. 129.5°–135.5°C. An analytical sample melts at 138.5°–139.5°C. after repeated crystallizations from 95% ethanol.

Analysis, Calcd. for $C_{17}H_{15}O_3NS$: C, 65.16; H, 4.83; N, 4.47.

Found: C, 64.88; H, 4.85; N, 4.11.

E. 3-Dimethylsulfamoyl-5H-dibenzo[a,d]cyclohepten-5-ol

3-Dimethylsulfamoyl-5H-dibenzo[a,d]cyclohepten-5-one (6.9 g., 0.022 mole) and 100 ml. of absolute methanol are stirred and heated to refluxing. A solution of 1.6 g. (0.0296 mole) of potassium borohydride in 12 ml. of water containing one pellet of potassium hydroxide is added dropwise at a rate such that reflux is maintained without external heating. After another 1½ hours at reflux, the solution is evaporated to dryness under reduced pressure. The residual white solid is suspended in water, collected, and crystallized from 95% ethanol. The yield of 3-dimethylsulfamoyl-5H-dibenzo[a,d]cyclohepten-5-ol is 6.05 g. (87%), m.p. 150°–152°C. The melting point is unchanged by further recrystallization.

Analysis, Calcd. for $C_{17}H_{17}O_3NS$: C, 64.74; H, 5.44; N, 4.44.

Found: C, 64.22; H, 5.44; N, 4.40.

F. 5-Chloro-3-dimethylsulfamoyl-5H-dibenzo[a,d]cycloheptene

A solution of 1.0 g. (0.00317 mole) of 3-dimethylsulfamoyl-5H-dibenzo[a,d]cyclohepten-5-ol in a mixture of 2 ml. of dry dioxane and 2 ml. of absolute ether is cooled in ice and saturated with dry hydrogen chloride. The mixture is allowed to stand at room temperature for 5 hours and then is refrigerated overnight. The white crystalline product is collected, washed with petroleum ether, and dried in a vacuum desiccator over calcium chloride. The yield of 5-chloro-3-dimethylsulfamoyl-5H-dibenzo[a,d]cycloheptene is 600 mg., m.p. 139.5°–143.5°C. Dilution of the mother liquor with petroleum ether gives a second crop which is recrystallized from a mixture of ether and petroleum ether affording 250 mg., m.p. 138.5°–142.5°C.

Analysis, Calcd. for $C_{17}H_{16}O_2NClS$: C, 61.16; H, 4.83; N, 4.20.

Found: C, 61.15; H, 4.57; N, 4.11.

G. 3-Dimethylsulfamoyl-5-(3-dimethylaminopropyl)-5H-dibenzo[a,d]cycloheptene

By replacing the 3,5-dichloro-5H-dibenzo[a,d]cycloheptene used in Example 17, Step A., with an equimolecular amount of 5-chloro-3-(dimethylsulfamoyl)-5H-dibenzo[a,d]cycloheptene and following substantially the same procedure described in Example 17, Step A., there is obtained 3-dimethylsulfamoyl-5-(3-dimethylaminopropyl)-5H-dibenzo[a,d]cycloheptene. The yield of yellow oily base is 50%.

H. 3-Dimethylsulfamoyl-5-(3-methylaminopropyl)-5H-dibenzo[a,d]cycloheptene

3-Dimethylsulfamoyl-5-(3-dimethylaminopropyl)-5H-dibenzo[a,d]cycloheptene is converted to the corresponding cyanamide by following the procedure of Example 17, Step B. The cyanamide (0.28 g., 0.00071 mole) together with 2.8 ml. of glacial acetic acid, 2.0 ml. of water and 0.4 ml. of concentrated hydrochloric acid is heated to refluxing for 29 hours. The reaction mixture is evaporated to dryness under reduced pressure and the residue is dissolved in water. The aqueous solution is made alkaline with sodium hydroxide and the oily base that separates is extracted into ether. The washed and dried ether extract is evaporated under reduced pressure, leaving 3-dimethylsulfamoyl-5-(3-methylaminopropyl)-5H-dibenzo[a,d]cycloheptene as an oil weighing 170 mg. The base may be converted to the hydrogen oxalate salt by dissolution in absolute ethanol, addition of an equimolar quantity of oxalic acid dissolved in ethanol, and precipitation by the addition of ether. After repeated recrystallizations from absolute ethanol and from isopropyl alcohol, the hydrogen oxalate melts at 133.5°–135.5°C., dec.

Analysis, Calcd. for $C_{21}H_{26}O_2N_2S \cdot C_2H_2O_4$: C, 59.98; H, 6.13; N, 6.08.

Found: C, 60.00; H, 6.42; N, 6.09.

EXAMPLE 19

3-Chloro-5-(3-methylaminopropylidene)-5H-dibenzo[a,d]cycloheptene hydrochloride (α- and β- isomers)

A. Preparation of 3-chloro-5-[3-(N-cyano-N-methyl-)aminopropylidene]-5H-dibenzo[a,d]cycloheptene A solution of 2.23 g. (0.0072 mole) of the β-isomer of 3-chloro-5-(3-dimethylaminopropylidene)-5H-dibenzo[a,d]cycloheptene in 4 ml. of dry benzene is added dropwise to a solution of cyanogen bromide (0.915 g., 0.0086 mole) in 3 ml. of dry benzene, while stirring and maintaining a slow stream of nitrogen through the apparatus. A solid separates and 4 ml. of benzene is added to facilitate stirring which is continued for 4 hours. The solid is removed by filtration through a sintered glass funnel and washed with benzene. Solvent and excess cyanogen bromide are evaporated from the combined filtrate and washings under reduced pressure. The residue is dissolved in 30 ml. of benzene and the solution washed with 1N hydrochloric acid and then with water. Evaporation of the benzene under reduced pressure gives 3-chloro-5-[3-(N-cyano-N-methyl)-aminopropylidene]-5H-dibenzo[a,d]cycloheptene as a white solid, m.p. 115°–118.5°C., in a yield of 1.9 g. (83%). An analytical sample melts at 117.5°–118°C. after recrystallization from cyclohexane.

Analysis, Calcd. for $C_{20}H_{17}N_2Cl$: C, 74.89; H, 5.34; N, 8.74. Found: C, 74.71; H, 5.23; N, 8.61.

B. 3-Chloro-5-(3-methylaminopropylidene)-5H-dibenzo[a,d]cycloheptene hydrochloride (α- and β- isomers)

3-Chloro-5-[3-(N-cyano-N-methyl)-aminopropylidene]-5H-dibenzo[a,d]cycloheptene (1.5 g., 0.00467 mole) and a solution of potassium hydroxide (16.7 g., 0.254 mole) in 25 ml. of absolute methanol are stirred and heated to refluxing for 48 hours. The cooled mixture is diluted with 70 ml. of water and the oil that separates is extracted into benzene. Evaporation of the washed and dried benzene extract under reduced pressure leaves an oil which then is dissolved in 70 ml. of absolute ether. The ethereal solution is filtered from a trace of flocculent precipitate and the ether is evaporated under reduced pressure. The 3-chloro-5-(3-methylaminopropylidene)-5H-dibenzo[a,d]cycloheptene is obtained as a yellow oily residue weighing 1.19 g. The product is converted to the hydrochloride by treating a solution of the base in 9 ml. of absolute ethanol with 1.17 ml. of 4.13N hydrogen chloride in absolute ethanol. The 3-chloro-5-(3- methylaminopropylidene)-5H-dibenzo[a,d]cycloheptene hydrochloride is separated into the α-and β- forms by fractional precipitation from the ethanolic solution with absolute ether. The α-form melts at 263°–265°C., dec. after repeated recrystallizations from a mixture of absolute ethanol and absolute ether.

Analysis, Calcd. for $C_{19}H_{18}NCl.HCl$: C, 68.68; H, 5.76; N, 4.22. Found: C, 68.60; H, 5.60; N, 4.16.

The β-form melts at 187°–189°C. (cloudy melt clear at 191°C.) after repeated recrystallization from ethanol - ether and isopropyl alcohol - ether mixtures.

Analysis, Calcd. for $C_{19}H_{18}NCl.HCl$: C, 68.68; H, 5.76; N, 4.22. Found: C, 68.00; H, 5.83; N, 3.91.

EXAMPLE 20

10-Bromo-5-(3-methylaminopropylidene)-5H-dibenzo[a,d]cycloheptene

A. 10-Bromo-5-(3-dimethylaminopropyl)-5-hydroxy-5H-dibenzo[a,d]cycloheptene

3-Dimethylaminopropylmagnesium chloride is prepared from 3.4 g. (0.14 g. atom) of magnesium and 17.0 g. (0.14 mole) of 3-dimethylaminopropyl chloride in 50 ml. of dry tetrahydrofuran, following the method of Example 9, Step A. A solution of 20.0 g. (0.07 mole) of 10-bromo-5H-dibenzo[a,d]cyclohepten-5-one in 40 ml. of tetrahydrofuran is added dropwise to the Grignard solution while cooling in an ice-bath and stirring over a period of 30 minutes. The mixture is allowed to warm up to room temperature and stirred for 2 hours. The bulk of the solvent then is distilled below 50°C. under reduced pressure, the residue dissolved in 50 ml. of benzene and the Grignard adduct hydrolyzed by the addition of 25 ml. of water to the solution while stirring and cooling. The benzene solution is separated from the magnesium slurry by decantation and the slurry extracted with additional portions of benzene. After washing with water, the benzene is distilled from the combined extracts to give 25.67 g. of a yellow oily residue. The residue is dissolved by warming in 350 ml. of 0.5N citric acid solution and the solution back-extracted with benzene. The acid extract is then rendered alkaline with sodium hydroxide and the base extracted into methylene chloride. After washing with water, the solvent is evaporated and the residue crystallized from a mixture of cyclohexane and hexane. The yield of white crystalline product, m.p. 118°–119.5°C. is 20 g. Recrystallization from hexane raises the m.p. to 118.5°–120°C.

Analysis, Calcd. for $C_{20}H_{22}BrNO$: C, 64.54; H, 5.96; N, 3.76. Found: C, 64.26; H, 5.93; N, 3.76.

B. 10-Bromo-5-(3-dimethylaminopropylidene)-5H-dibenzo[a,d]cycloheptene

10-Bromo-5-(3-dimethylaminopropyl)-5-hydroxy-5H-dibenzo[a,d]cycloheptene (14.75 g., 0.0396 mole) is dissolved in 100 ml. of trifluoroacetic acid. Trifluoroacetic anhydride, 50 ml., is added and the solution heated to refluxing with stirring for 1½ hours. The excess trifluoroacetic anhydride and the trifluoroacetic acid are distilled, the residue suspended in water and the mixture rendered alkaline with sodium hydroxide solution. The base is extracted into ether. After washing the extract with water, the ether is distilled, leaving the oily product as the residue in a yield of 13.75 g. (98%).

C. 10-Bromo-5-[3-(N-cyano-N-methyl)-aminopropylidene]-5H-dibenzo[a,d]cycloheptene 10-Bromo-5-(3-dimethylaminopropylidene)-5H-dibenzo[a,d]cycloheptene (2.83 g., 0.008 mole) in 2 ml. of dry benzene is added dropwise to a solution of 1.02 g. (0.0096 mole) of cyanogen bromide in 4 ml. of benzene while stirring and maintaining the temperature at 25°–30°C. A slow stream of nitrogen is swept through the apparatus throughout the addition. After the addition is complete the mixture is stirred for 4 hours, then allowed to stand 15 hours at room temperature. The solvent is distilled under reduced pressure. The residue is taken up in methylene chloride and taken to dryness again. The residue then is dissolved in methylene chloride and the solution extracted with 1N hydrochloric acid. After washing with water, the methylene chloride solution is dried over sodium sulfate and evaporated to give 2.15 g. of the product as an oily residue.

D. 10-Bromo-5-(3-methylaminopropylidene)-5H-dibenzo[a,d]cycloheptene

10-Bromo-5-[3-(N-cyano-N-methyl)-aminopropylidene]-5H-dibenzo[a,d]cycloheptene (2.0 g., 0.00548 mole) is dissolved in 40 ml. of glacial acetic acid. Water, 27 ml., and concentrated hydrochloric acid, 4 ml., are added and the mixture is heated to refluxing with stirring for 17 hours. The bulk of the solvent is distilled under reduced pressure and the residue is dissolved in 65 ml. of water and the solution extracted with benzene. The aqueous layer is rendered alkaline with sodium hydroxide and the product is extracted into benzene. After washing with water, the benzene is distilled, leaving the mixed geometric isomers of 10-bromo-5-(3-methylaminopropylidene)-5H-dibenzo[a,d]cycloheptene as a yellow oily residue in a yield of 1.86 g.

E. 10-Bromo-5-(3-methylaminopropylidene)-5H-dibenzo[a,d]cycloheptene hydrogen maleate (α-isomer)

A 1.65 g. (0.00485 mole) portion of the product of Step D. is dissolved in 15 ml. of absolute alcohol. A solution of maleic acid (0.620 g., 0.00533 mole) in absolute alcohol (4 ml.) is added and the solution diluted with absolute ether to incipient cloudiness. A first crop of crystals weighing 0.55 g. is collected. This material sintered at 153.5°C. and melted at 159°C. A second crop of product weighing 0.25 g., m.p. 151.5°–155.5°C., is obtained from the mother liquors. The combined products are recrystallized three times from methanol - ether mixtures to give material with a constant m.p. of 166°–167.5°C.

Analysis, Calcd. for $C_{19}H_{18}BrN.C_4H_4O_4$: C, 60.53; H, 4.86; N, 3.07. Found: C, 60.75; H, 4.95; N, 2.90.

F. 10-Bromo-5-(3-methylaminopropylidene)-5H-dibenzo[a,d]cycloheptene hydrogen oxalate (β-isomer)

The mother liquors from another experiment such as (E) are concentrated and amorphous hydrogen maleate of the β-isomer is converted to the base. The base, 10.8 g., is dissolved in 20 ml. of benzene and 10 ml. of the solution applied to each of two chromatography columns constructed of polyethylene tubing, 2 cm. in diameter and packed with 60 g. of alumina (Merck, reagent) activated in situ by means of acetone. Each column is developed by passing 100 ml. of chloroform through it. The columns then are slit longitudinally. A zone is visible approximately ⅓ of the distance from the top of the adsorbent. The section of the column below this zone is removed and eluted with boiling methanol. After separating the solid, the methanol is distilled, leaving 1.66 g. of a yellow oily residue. A 0.49 g. (0.00144 mole) portion of this base is dissolved in 10 ml. of absolute ethanol and treated with a solution of 0.142 g. (0.00158 mole) of oxalic acid in 5 ml. of absolute methanol. The hydrogen oxalate salt of the product separates as a pale yellow solid. Three recrystallizations from absolute ethanol give product, m.p. 219°–220°C.

Analysis: Calcd, for $C_{19}H_{18}BrN.C_2H_2O_4$: C, 58.61; H, 4.69; N, 3.26. Found: C, 58.82; H, 4.71; N, 3.23.

EXAMPLE 21

10-Chloro-5H-dibenzo[a,d]cyclohepten-5-one

A. Phosphorus pentachloride addition complex of 5H-dibenzo[a,d]cyclohepten-5-one To a solution of 25.0 g. of 10,11-dihydro-5H-dibenzo[a,d]cyclohepten-5-one in 2.5 ml. phosphorus oxychloride and 50 ml. dry benzene is added 75 g. phosphorus pentachloride (3 eq.) and the mixture is stirred under reflux for 2.5 hours with protection from moisture. After ca. 15 minutes a clear red solution results and a crystalline complex slowly separates accompanied by evolution of hydrogen chloride. At the end of the reflux period the reaction mixture is chilled to 10°C. and the dark red complex is isolated by filtration and washed twice with 25 ml. of dry benzene.

B. 10-Chloro-5H-dibenzo[a,d]cyclohepten-5one 0.5 G. of the phosphorus addition complex prepared above is heated for 1 hour at 100°C. in vacuum. The cooled reaction product is then triturated with acetic acid to deposit 10-chloro-5H-dibenzo[a,d]cyclohepten-5-one, m.p. 118°–121°C.; on recrystallization from methanol, m.p. 125°–126°C.

EXAMPLE 22

5-(3-Cyclopropylaminopropyl)-5H-dibenzo[a,d]cycloheptene 5-(3-Iodopropyl)-5H-dibenzo[a,d]cycloheptene, 3.6 g. (0.01 mole), is dissolved in 15 ml. of absolute ethanol. Cyclopropylamine, 3 ml., is added and the mixture allowed to stand overnight at room temperature. Ethanol is evaporated under reduced pressure and the residual solid treated with aqueous sodium hydroxide and extracted into benzene. After washing with water, the benzene layer is shaken thoroughly with several portions of 3 N hydrochloric acid and again washed with water. Evaporation of the benzene under reduced pressure and crystallization of the residual oily solid from a mixture of isopropyl alcohol and absolute ether gives 5-(3-cyclopropylaminopropyl)-5H-dibenzo[a,d]cycloheptene hydrochloride as white crystals, m.p. 212°–213°C., in a yield of 650 mg. (20%). Recrystallization from a mixture of isopropyl alcohol and absolute ether affords an analytical sample, m.p. 211°–212°C.

Analysis, Calcd. for $C_{21}H_{23}N.HCl$: C, 77.39; H, 7.42; N, 4.30. Found: C, 77.15; H, 7.36; N, 4.29.

EXAMPLE 23

5-(3-Dimethylaminopropylidene)-3-methylsulfonyl-5H-dibenzo[a,d]cycloheptene

A. Preparation of cuprous methylmercaptide

Concentrated ammonium hydroxide solution, 300 ml., is placed in a 1 liter, 3-necked flask fitted with a stirrer and gas inlet tube. The apparatus is cooled in an ice-bath and flushed with dry nitrogen while 40.0 g. (0.40 mole) of cuprous chloride is added portion-wise with stirring. To the dark blue solution is added 95% ethanol, 300 ml., and then methylmercaptan is bubbled into the cooled solution until precipitation is complete and the supernatant solution becomes yellow. The solid is collected and washed by centrifugation with four portions of dilute ammonium hydroxide solution, followed by four portions of absolute ethanol. The yellow product is dried under reduced pressure at 45°–50°C. and finally in a vacuum dessicator over concentrated sulfuric acid. The yield of product is 41.4 g. (93%).

B. Preparation of 3-methylmercapto-5H-dibenzo[a,d]cyclohepten-5-one

3-Bromo-5H-dibenzo[a,d]cyclohepten-5-one, 7.93 g. (0.028 mole), and cuprous methylmercaptide, 4.01 g. (0.036 mole), prepared as described in Step A., are put in a 100 ml. flask fitted with a stirrer and reflux condenser. Quinoline, 44.8 ml., and pyridine, 4.0 ml., are added and the slurry is heated at 200°C. with stirring for 6 hours. The reaction mixture is poured into 6 N. hydrochloric acid, 120 ml., and ice and extracted with five 150 ml. portions of boiling benzene. The combined extracts are washed with three 200 ml. portions of 3 N. hydrochloric acid. After washing with water, the solvent is evaporated under reduced pressure leaving a brown oil, weight 7.41 g., as residue. The oil is dissolved in absolute methanol, 125 ml., and boiled with 370 mg. decolorizing carbon for 30 minutes. The filtrate is concentrated to 60 ml. and a yellow solid separates, along with a brown oil. The solid is mechanically separated from the oil and dried in a vacuum dessicator over concentrated sulfuric acid. The product weighs 2.77 g. and melts at 66.5°–67.5°C. The brown oil is evaporatively distilled at 146°C./0.1 mm. and the sublimate is crystallized from 25 ml. of absolute methanol to give 2.65 g. of material melting at 66.5°–67.5°C. (77% yield).

Analysis, Calcd. for $C_{16}H_{12}OS$: C, 76.16; H, 4.80; S, 12.71. Found: C, 76.35; H, 4.61; S, 12.60.

C. Preparation of 5-(3-dimethylaminopropyl)-5-hydroxy-3-methylmercapto-5H-dibenzo[a,d]cycloheptene The Grignard reagent is prepared from 4.86 g. (0.2 g. atom) of magnesium and 24.34 g. (0.2 mole) of 3-dimethylaminopropyl chloride in 100 ml. of tetrahydrofuran as described in U.S. Pat. No. 3,046,283, Step A of Example 2. The solution is standardized by determination of the magnesium content. A volume of the solution containing 0.043 mole of Grignard reagent is cooled in an ice-bath and stirred while a solution of 3-methylmercapto-5H-dibenzo[a,d]cyclohepten-5-one, 5.38 g. (0.0213 mole) in 28 ml. tetrahydrofuran, is added over a period of 20 minutes. The reaction mixture is stirred in an ice-bath for 30 minutes and at room temperature for ninety minutes. The bulk of the solvent is then distilled at 45°C. under reduced pressure and benzene, 70 ml., is added to the residue. The solution is cooled in an ice-bath and the Grignard adduct is hydrolyzed by the dropwise addition of water, 20 ml., with stirring. The benzene solution is separated and the gelatinous residue is extracted three times with 50 ml. portions of boiling benzene. The combined benzene extracts are extracted with three 45 ml. portions of 0.5 M. citric acid solution and washed once with 50 ml. $H_2O$. The combined aqueous solutions are made basic with sodium hydroxide solution and extracted with ether. The combined extracts are washed with water and evaporated under reduced pressure. The yellow solid residue, m.p. 127°–129°C., weighs 6.88 g. (95%).

Recrystallization from ethanol-water yields 6.50 g. of product melting at 128°–129°C.

Analysis, Calcd. for $C_{21}H_{25}NOS$: C, 74.29; H, 7.42; N, 4.13. Found: C, 74.60; H, 7.56; N, 3.94.

D. Preparation of 5-(3-dimethylaminopropyl)-5-hydroxy-3-methylsulfonyl-5H-dibenzo[a,d]cycloheptene 5-(3-Dimethylaminopropyl)-5-hydroxy-3-methylmercapto-5H-dibenzo[a,d]cycloheptene, 21.53 g. (0.063 mole), is dissolved in glacial acetic acid, 250 ml., and the solution is cooled in an ice-bath while 30% hydrogen peroxide, 25.8 ml., is added dropwise with stirring. After standing at room temperature for twenty-two hours, the solution is saturated with sulfur dioxide for 1 hour with periodic cooling in an ice-bath. The solution is made basic with 10 N. sodium hydroxide solution, 625 ml., and extracted with three 300 ml. portions of benzene. After washing the combined extracts with water, solvent is distilled under reduced pressure leaving a yellow oily residue, weight 23.20 g. The oil solidifies on standing at room temperature. Four recrystallizations from methanol-water gives 13.22 g. (57%) of product melting at 170.5°–171.5°C.

Analysis, Calcd. for $C_{21}H_{25}NO_3S$: C, 67.89; H, 6.78; N, 3.77. Found: C, 67.72; H, 6.78; N, 3.59.

E. 5-(3-Dimethylaminopropylidene)-3-methylsulfonyl-5H-dibenzo[a,d]cycloheptene (mixed geometric isomers)

5-(3-Dimethylaminopropyl)-5-hydroxy-3-methylsulfonyl-5H-dibenzo[a,d]cycloheptene (13.62 g., 0.037 mole) is dissolved in 136 ml. of trifluoroacetic acid. Trifluoroacetic anhydride, 68 ml., is added and the solution heated under reflux for 1 hour in a water-bath at 70°C. The dark green solution is cooled and poured into 250 ml. of ice-water. The mixture is rendered alkaline with 10 N. sodium hydroxide solution while stirring and cooling and extracted with benzene. The benzene extract is washed with water, dried over sodium sulfate and the benzene distilled under reduced pressure. The mixed geometric isomers of 5-(3-dimethylaminopropylidene)-3-methylsulfonyl-5H-dibenzo[a,d]cycloheptene is obtained as a brown oily residue in a yield of 13.19 g. (theory, 13.08 g.).

F. α-Isomer of 5-(3-dimethylaminopropylidene)-3-methylsulfonyl-5H-dibenzo[a,d]cycloheptene Hydrochloride The mixture of geometric isomers is dissolved in alcohol. One-half molar equivlent of dry hydrogen chloride dissolved in absolute alcohol is added and the solvent evaporated on a water-bath under reduced pressure. The residue is taken up in isopropyl alcohol and an equal volume of acetone is added. Absolute ether then is added to incipient cloudiness. The α-isomer separates as the crystalline hydrochloride, and is recrystallized to constant melting point. In one experiment the product so obtained sintered at 217°C. and melted at 218.5°–219.5°C., clearing at 220.5°C.

Analysis, Calcd. for $C_{21}H_{23}O_2S.HCl$: HCl: C, 64.68; H, 6.20; N, 3.59; Cl, 9.09. Found: C, 64.32; H, 6.35; N, 3.38; Cl, 8.78.

G. β-Isomer of 5-(3-dimethylaminopropylidene)-3-methylsulfonyl-5H-dibenzo[a,d]cycloheptene The mother liquors from the separation of the hydrochloride of the α-isomer are evaporated and treated with one-quarter of a molar equivalent of hydrogen chloride in absolute alcohol. After evaporating the solvent, the residue is treated with isopropyl alcohol and acetone and another crop of solid precipitates with ether as described in Step F. The mother liquors then are evaporated under reduced pressure and the residue shaken with dilute sodium hydroxide and benzene. The benzene layer is separated, washed with water and the benzene distilled under reduced pressure. The base of the β-isomer is covered with hexane and allowed to stand until partially crystalline. The base then is recrystallized to constant melting point from cyclohexane. The product obtained in a typical experiment sintered at 141°C., melted at 142.5°–143°C., clearing at 144°C.

Analysis, Calcd. for $C_{21}H_{23}NO_2S$: C, 71.36; H, 6.56; N, 3.96. Found: C, 71.37; H, 6.52; N, 3.97.

EXAMPLE 24

5-(3-Methylaminopropylidene)-3-methylsulfonyl-5H-dibenzo[a,d]cycloheptene (α-isomer)

By substituting 5-(3-dimethylaminopropylidene)-3-methylsulfonyl-5H-dibenzo[a,d]cycloheptene (α-isomer), product of Example 23, Step F.), for the 5-(3-dimethylaminopropylidene)-5H-dibenzo[a,d]cycloheptene of Example 6, and following substantially the procedure of Example 6, Steps A and B, 5-(3-methylaminopropylidene)-3-methylsulfonyl-5H-dibenzo[a,d]cycloheptene (α-isomer) is obtained in the form of a yellow oil. The product is converted to the hydrochloride that melts at 273°–274.5°C. (sintered, 271.5°C.) after recrystallization from mixtures of methanol and ether.

Analysis, Calcd. for $C_{20}H_{21}NO_2S.HCl$: C, 63.90; H, 5.90; N, 3.73; Cl, 9.43. Found: C, 63.67; H, 5.72; N, 3.59; Cl, 9.36.

EXAMPLE 25

5-(3-Methylaminopropylidene)-3-methylsulfonyl-5H-dibenzo[a,d]cycloheptene (β-isomer)

By substituting 5-(3-dimethylaminopropylidene)-3-methylsulfonyl-5H-dibenzo[a,d]cycloheptene (β-isomer), (Product of Example 23, Step G), for the 5-(3-dimethylaminopropylidene)-5H-dibenzo[a,d]cycloheptene of Example 6, and following substantially the procedure of Example 6, Steps A and B, 5-(3-methylaminopropylidene)-3-methylsulfonyl-5H-dibenzo[a,d]cycloheptene (β-isomer) is obtained in the form of a yellow oil. The product is converted to the hydrogen maleate that melts at 175°–176°C.

Analysis, Calcd. for $C_{20}H_{21}NO_2S.C_4H_4O_4$: C, 63.28; H, 5.53; N, 3.08. Found: C, 63.20; H, 5.39; N, 2.98.

EXAMPLE 26

10,11-Dihydro-5-(3-methylaminopropylidene)-3-methylsulfonyl-5H-dibenzo[a,d]cycloheptene (α-isomer)

A. Hydrogenation of 5-(3-dimethylaminopropylidene)-3-methylsulfonyl-5H-dibenzo[a,d]cycloheptene (α-isomer)

5-(3-Dimethylaminopropylidene)-3-methylsulfonyl-5H-dibenzo[a,d]cycloheptene (α-isomer), (1.39 g., 0.0039 mole), dissolved in 20 ml. of ethanol, is hydrogenated over Raney nickel at 65°C. under an initial hydrogen pressure of 440 p.s.i. The catalyst is separated and the solvent evaporated under reduced pressure. Recrystallization from cyclohexane gives 10,11-dihydro-5-(3-dimethylaminopropylidene)-3-methylsulfonyl-5H-dibenzo[a,d]cycloheptene (α-isomer), m.p. 121°–121.5°C. (sintered, 120°C.; cleared, 122.5°C.).

Analysis, Calcd. for $C_{21}H_{25}NO_2S$: C, 70.95; H, 7.09; N, 3.94. Found: C, 70.75; H, 7.13; N, 3.84.

B. Demethylation of 10,11-dihydro-5-(3-dimethylaminopropylidene)-3-methylsulfonyl-5H-dibenzo[a,d]cycloheptene (α-isomer)

By substituting 10,11-dihydro-5-(3-dimethylaminopropylidene)-3-methylsulfonyl-5H-dibenzo[a,d]cycloheptene (α-isomer) for the 5-(3-dimethylaminopropylidene)-5H-dibenzo[a,d]cycloheptene of Example 6, and following substantially the procedure of Example 6, Steps A and B, 10,11-dihydro-5-(3-methylaminopropylidene)-3-methylsulfonyl-5H-dibenzo[a,d]cycloheptene (α-isomer) is obtained as a yellow oil. The product is converted to the hydrochloride that melts at 275.5°–276.5°C. (sintered, 274.5°C.) after recrystallization from methanol-ether mixtures.

Analysis, Calcd. for $C_{20}H_{23}NO_2S \cdot HCl$: C, 63.56; H, 6.40; N, 3.71. Found: C, 63.79; H, 6.22; N, 3.66.

EXAMPLE 27

10,11-Dihydro-5-(3-methylaminopropylidene)-3-methylsulfonyl-5H-dibenzo[a,d]cycloheptene (β-isomer)

A. Hydrogenation of 5-(3-dimethylainopropylidene)-3-methylsulfonyl-5H-dibenzo[a,d]cycloheptene (β-isomer)

The procedure of Example 26, Step A, is employed using the β-isomer instead of the α-isomer. The β-isomer of 10,11-dihydro-5-(3-dimethylaminopropylidene)-3-methylsulfonyl-5H-dibenzo[a,d]cycloheptene is obtained as the crystalline base, m.p. 109°–110°C. (sintered, 108.5°C., cleared 110.5°C.).

Analysis, Calcd. for $C_{21}H_{25}NO_2S$: C, 70.95; H, 7.09; N, 3.94. Found: C, 71.20; H, 6.97; N, 3.88.

B. Demethylation of 10,11-dihydro-5-(3-dimethylaminopropylidene)-3-methylsulfonyl-5H-dibenzo[a,d]cycloheptene (β-isomer)

By substituting 10,11-dihydro-5-(3-dimethylaminopropylidene)-3-methylsulfonyl-5H-dibenzo[a,d]cycloheptene (β-isomer) for the 5-(3-dimethylaminopropylidene)-5H-dibenzo[a,d]cycloheptene of Example 6, and following substantially the procedure of Example 6, Steps A and B, 10,11-dihydro-5-(3-methylaminopropylidene)- 3-methylsulfonyl-5H-dibenzo[a,d]cycloheptene (β-isomer) is obtained in the form of a yellow oil. The product is converted to the hydrochloride that melts at 232.5°–234.5°C. after recrystallization from isopropyl alcohol.

Analysis, Calcd. for $C_{20}H_{23}NO_2S \cdot HCl$: C, 63.56; H, 6.40; N, 3.71. Found: C, 63.49; H, 6.30; N, 3.66.

EXAMPLE 28

5-(3-Methylaminopropyl)-3-methylsulfonyl-5H-dibenzo[a,d]cycloheptene

A. 3-Methylmercapto-5H-dibenzo[a,d]cyclohepten-5-ol

3-Methylmercapto-5H-dibenzo[a,d]cyclohepten-5-one, 27.9 g. (0.11 mole), is dissolved in 500 ml. of methanol. The solution is stirred and heated to refluxing while a solution of 14.9 g. (0.276 mole) of potassium borohydride in 150 ml. of water containing 0.2 ml. of 10 N. sodium hydroxide is added dropwise. After stirring at reflux for 2 hours, the solution is chilled and the precipitated product collected and washed with methanol yielding, typically, 27 g. (96%). An analytical sample melts at 117°–118.5°C. after repeated recrystallizations from methanol.

Analysis. Calcd. for $C_{16}H_{14}OS$: C, 75.58, H, 5.55; Found: C, 74.70; H, 5.56.

B. 5-Chloro-3-methylmercapto-5H-dibenzo[a,d]cycloheptene

A solution of 18 g. (0.071 mole) of 3-methylmercapto-5H-dibenzo[a,d]cyclohepten-5-ol in 90 ml. of dry dioxane is cooled in an ice-bath and saturated with dry hydrogen chloride. A solid separates and when precipitation appears to be complete, the mixture is stirred with 150 ml. of petroleum ether and the product collected, washed with petroleum ether, and dried in a vacuum desiccator over potassium hydroxide. The yield of 5-chloro-3-methylmercapto-5H-dibenzo[a,d]cycloheptene is 16 g. (84%), m.p. 135°–138°C. The melting point is unchanged by recrystallization from cyclohexane.

Analysis, Calcd. for $C_{16}H_{13}ClS$: C, 70.44; H, 4.80. Found: C, 70.19; H, 4.81.

C. 5-(3-Dimethylaminopropyl)-3-methylmercapto-5H-dibenzo[a,d]cycloheptene

The Grignard reagent is prepared from dimethylaminopropyl chloride (0.2 mole) and magnesium (0.2 g. atom) in 75 ml. of dry tetrahydrofuran following the method described in U.S. Pat. No. 2,996,503. A 15 ml. portion of this solution is cooled in an ice-bath and stirred while a solution of 4.7 g. (0.0172 mole) of 5-chloro-3-methylmercapto-5H-dibenzo[a,d]cycloheptene in 25 ml. of tetrahydrofuran is added dropwise. The usual precautions, such as careful drying of the apparatus and maintaining a nitrogen atmosphere, are observed. After stirring the mixture for 2 hours at room temperature, the bulk of the solvent is distilled at 30°C. under reduced pressure and the residue dissolved in benzene. The solution is cooled in an ice-bath and the excess Grignard reagent hydrolyzed by the dropwise addition of water. The benzene layer is decanted and the gelatinous precipitate washed with four 25 ml. portions of boiling benzene. After washing with water, the combined benzene solutions are extracted with 50 ml. of 0.5 M. citric acid. The acid extract is rendered alkaline with sodium hydroxide and the oily base extracted into benzene. Evaporation of the washed benzene extract under reduced pressure leaves 5-(3-dimethylaminopropyl)-3-methylmercapto-5H-dibenzo[a,d]cycloheptene as the oily residue weighing, typically, 4.2 g. (75%).

D. 5-(3-Dimethylaminopropyl)-3-methylsulfonyl-5H-dibenzo[a,d]cycloheptene 5-(3-Dimethylaminopropyl)-3-methylmercapto-5H-dibenzo[a,d]cycloheptene, 1.6 g. (0.005 mole), is dissolved in 16 ml. of glacial acetic acid. The solution is cooled in an ice-bath to 15°C. and stirred while hydrogen peroxide, 2 ml. of 30%, is added dropwise. The ice-bath then is removed and the solution stirred while it warms to room temperature and then allowed to stand for 65 hours. The solution is cooled in an ice-bath and stirred while sulfur dioxide is introduced for 1 hour. After dilution with an equal volume of water and with stirring and cooling, the mixture is rendered alkaline with sodium hydroxide and the oily base extracted into benzene. Solvent is evaporated from the washed benzene extract under reduced pressure, leaving the product as a viscous oily residue in a yield of 1.75 g. (93%). The base may be converted to the hydrogen oxalate salt by treating a solution in ethanol with an equimolar quantity of oxalic acid dissolved in ethanol. 5-(3-Dimethylaminopropyl)-3-methylsulfonyl-5H-dibenzo[a,d]cycloheptene hdyrogen oxalate separates as a white crystalline solid, m.p. 191°–192°C. dec. The melting point is unchanged by recrystallization from ethanol.

Analysis, Calcd. for $C_{21}H_{25}NO_2S\cdot C_2H_2O_4$: C, 62.00; H, 6.11; N, 3.15. Found: C, 61.74; H, 5.95; N, 3.07.

E. 5-(3-Methylaminopropyl)-3-methylsulfonyl-5H-dibenzo[a,d]cycloheptene

By substituting 5-(3-dimethylaminopropyl)-3-methylsulfonyl-5H-dibenzo[a,d]cycloheptene for the 5-(3-dimethylaminopropylidene)-5H-dibenzo[a,d]cycloheptene of Example 6, Step A, and following substantially the same procedure described in Example 6, Steps A and B, there is obtained 5-(3-methylaminopropyl)-3-methylsulfonyl-5H-dibenzo[a,d]cycloheptene as an oily residue. The base is converted to the hydrogen oxalate salt by treating an ethanolic solution of the base with a 10% excess of oxalic acid in ethanol. Dilution with absolute ether precipitates 5-(3-methylaminopropyl)-3-methylsulfonyl-5H-dibenzo[a,d]-cycloheptene hydrogen oxalate as a white crystalline solid, m.p. 114°–119°C. dec. An analytical sample melts at 114°–115°C. dec. after two recrystallizations from mixtures of absolute ethanol and absolute ether.

Analysis, Calcd. for $C_{20}H_{23}NO_2S\cdot C_2H_2O_4$: C, 61.24; H, 5.84; N, 3.25. Found: C, 61.39; H, 6.07; N, 3.14.

We claim:

1. A compound selected from the group consisting of:

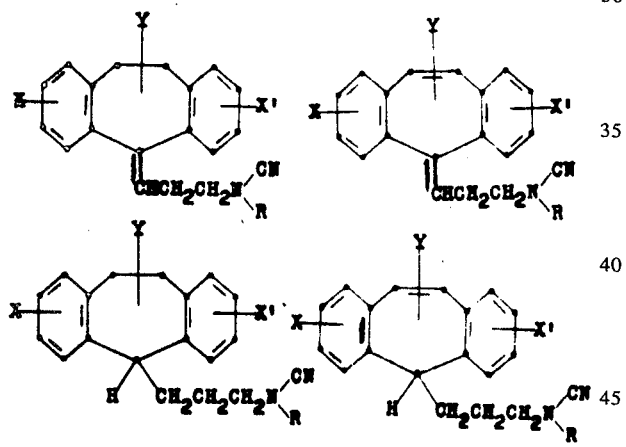

wherein R is a lower alkyl radical, Y is selected from the group consisting of hydrogen and halogen and X and X' are selected from the group consisting of hydrogen, an alkyl group having up to 6 carbon atoms, an alkenyl group having up to 6 carbon atoms, a perfluoroalkyl group having up to 4 carbon atoms, phenyl, an acyl group having up to 4 carbon atoms, a perfluoroacyl group having up to 4 carbon atoms, amino, an alkylamino group having up to 4 carbon atoms, a dialkylamino group having up to 8 carbon atoms, an acylamino group having up to 4 carbon atoms, a perfluoroacylamino group having up to 4 carbon atoms, an alkylsulfonylamino group having up to 4 carbon atoms, halogen, hydroxyl, an alkoxyl group having up to 4 carbon atoms, a perfluoroalkoxyl group having up to 4 carbon atoms, cyano carboxy, carbenyl, an alkylcarbamyl group having up to 5 carbon atoms, a dialkylcarbamyl group having up to 9 carbon atoms, a carbalkoxy group having up to 6 carbon atoms, mercapto, an alkylmercapto group having up to 4 carbon atoms, a perfluoroalkylmercapto group having up to 4 carbon atoms, an alkylsulfonyl group having up to 4 carbon atoms, a perfluoroalkylsulfonyl group having up to 4 carbon atoms, sulfamoyl, an alkylsulfamoyl group having up to 4 carbon atoms and a dialkylsulfamoyl group having up to 8 carbon atoms.

2. A 5-(3-N-cyano-N-lower alkylaminopropylidene)-5H-dibenzo[a,d]cycloheptene.

3. A 5-(3-N-cyano-N-lower alkylaminopropylidene)-10,11-dihydro-5H-dibenzo[a,d]cycloheptene.

4. A 5-(3-N-cyano-N-lower alkylaminopropyl)-5H-dibenzo[a,d]cycloheptene.

5. A 5-(3-N-cyano-N-lower alkylaminopropyl)-10,11-dihydro-5H-dibenzo[a,d]cycloheptene.

6. 5-(3-N-Cyano-N-methylaminopropyl)-5H-dibenzo-[a,d]cycloheptene.

7. 5-(3-N-Cyano-N-methylaminopropylidene)-10,11-dihydro-5H-dibenzo[a,d]cycloheptene.

\* \* \* \* \*

UNITED STATES PATENT OFFICE
CERTIFICATE OF CORRECTION

PATENT NO. : 3,978,121
DATED : August 31, 1976
INVENTOR(S) : Edward L. Engelhardt It is certified that error appears in the above-identified patent and that said Letters Patent are hereby corrected as shown below:

Claim 1, column 38, line 16, "carbenyl" should be -- carbamyl --.

Signed and Sealed this

Sixteenth Day of November 1976

[SEAL]

Attest:

RUTH C. MASON
Attesting Officer

C. MARSHALL DANN
Commissioner of Patents and Trademarks